(12) United States Patent
Sato et al.

(10) Patent No.: US 8,449,116 B2
(45) Date of Patent: May 28, 2013

(54) ELECTRO-OCULOGRAPHY ESTIMATING DEVICE, ELECTRO-OCULOGRAPHY CALCULATING METHOD, EYE-GAZE TRACKING DEVICE, WEARABLE CAMERA, HEAD-MOUNTED DISPLAY, AND ELECTRONIC EYEGLASSES

(75) Inventors: Daisuke Sato, Osaka (JP); Toshiyasu Sugio, Osaka (JP)

(73) Assignee: Panasonic Corporation, Osaka (JP)

( * ) Notice: Subject to any disclaimer, the term of this patent is extended or adjusted under 35 U.S.C. 154(b) by 275 days.

(21) Appl. No.: 12/947,908

(22) Filed: Nov. 17, 2010

(65) Prior Publication Data

US 2011/0178784 A1    Jul. 21, 2011

(30) Foreign Application Priority Data

Nov. 18, 2009   (JP) ................................ 2009-262679

(51) Int. Cl.
*A61B 3/14*   (2006.01)
*A61B 3/10*   (2006.01)
*A61B 3/113*  (2006.01)
*A61B 3/107*  (2006.01)

(52) U.S. Cl.
CPC ............... *A61B 3/113* (2013.01); *A61B 3/107* (2013.01)
USPC ............ 351/209; 351/210; 351/212; 351/246

(58) Field of Classification Search
CPC ................................ A61B 3/113; A61B 3/107
USPC ..................... 351/204–206, 209–212, 246
See application file for complete search history.

(56) References Cited

U.S. PATENT DOCUMENTS

2004/0174496 A1*   9/2004   Ji et al. ..................... 351/209
2009/0109400 A1*   4/2009   Yoshinaga et al. ............ 351/210

OTHER PUBLICATIONS

Nobuyuki Itsuki, et al. "A Battery Model of the Eyeball to Calculate Standing Potential of the Eye", Journal of Japanese Ophthalmological Society, vol. 99, No. 9, pp. 1012-1016, Sep. 10, 1995 with English translation.

* cited by examiner

*Primary Examiner* — Huy K Mai
(74) *Attorney, Agent, or Firm* — Wenderoth, Lind & Ponack, L.L.P.

(57) ABSTRACT

An electro-oculography estimating device includes: a distance obtaining unit which obtains a right-eye corneal distance, a right-eye retinal distance, a left-eye corneal distance, and a left-eye retinal distance; and an electro-oculography theoretical value calculating unit which calculates an electro-oculography theoretical value generated at the given three-dimensional positions, based on the right-eye corneal distance, the right-eye retinal distance, the left-eye corneal distance, and the left-eye retinal distance that are obtained by the distance obtaining unit, as an input into an electro-oculography model that is a function for calculating the electro-oculography theoretical value generated in the given three-dimensional spatial position, based on the right-eye corneal distance, the right-eye retinal distance, the left-eye corneal distance, and the left-eye retinal distance.

20 Claims, 28 Drawing Sheets

FIG. 10

| Electro-oculography change amount | Eyeball movement angle |
|---|---|
| 5V | 40° |
| 4.5V | 30° |
| 4V | 20° |
| ⋮ | |
| -5V | -40° |

FIG. 11

| Electro-oculography change amount | Gaze position |
|---|---|
| 5V | (600,0) |
| 4.5V | (500,0) |
| 4V | (400,0) |
| ⋮ | |
| -5V | (-600,0) |

ELECTRO-OCULOGRAPHY ESTIMATING DEVICE, ELECTRO-OCULOGRAPHY CALCULATING METHOD, EYE-GAZE TRACKING DEVICE, WEARABLE CAMERA, HEAD-MOUNTED DISPLAY, AND ELECTRONIC EYEGLASSES

BACKGROUND OF THE INVENTION (1) Field of the Invention

The present invention relates to an electro-oculography estimating device, an electro-oculography calculating method, an to eye-gaze tracking device, a wearable camera, a head-mounted display, and electronic eyeglasses.

(2) Description of the Related Art

Conventionally, an eye-gaze tracking technique using Electro-oculography (EOG) is well known. The technique is to detect an eye-gaze by measuring eye potential (electro-oculogram) generated by a positive charge in a cornea and a negative charge in a retina, using a plurality of electrodes attached around eyes. Unlike an eye-gaze tracking technique for capturing an image of an eyeball using a camera, this technique using EOG has such advantages as not interfering with vision, not being influenced by outside light, not depending on a shape and an opening state of the eye, and achieving low power consumption, and thus is expected to be applied to various devices.

However, while the conventional eye-gaze tracking technique using EOG performs linear approximation on a relationship between the gaze and EOG, EOG that is actually measured becomes more nonlinear when a gaze angle is larger. For this reason, the conventional eye-gaze tracking technique using EOG has low accuracy in gaze detection (gaze error 5° to 10°).

<Battery Model of Eyeballs>

Thus, Non-Patent Reference 1 discloses a nonlinear model of EOG. Non-Patent Reference 1 suggests a model (battery model) which assumes the cornea of an eyeball as a plus battery and the retina as a minus battery, and uses a battery rotation to resemble eyeball movement. When r and r' represent distances from an electrode to the cornea center and the retina center, respectively, I is a current flowing from the retina to the cornea within the eyeball, and σ is conductivity around the eyeball, potential v generated at the electrode is calculated in accordance with (Expression 1) below:

(Expression 1)

$$v = \frac{J}{4\pi\sigma}\left(\frac{1}{r} - \frac{1}{r'}\right) \quad [\text{Math 1}]$$

This shows a possibility of evaluating EOG in a mathematical expression, and describes the method as effective for clinical application in the future (as an electrophysiological method for obtaining information from eye fundus that cannot be visually obtained, estimation of visual impairment, or the like).

PATENT REFERENCE

Non-Patent Reference

[Non-Patent Reference 1]

Itsuki, et al. "A Battery Model of the Eyeball to Calculate Standing Potential of the Eye", Journal of Japanese Ophthalmological Society Vol. 99, No. 9, pp. 1012-1016, Sep. 10, 1995

However, Non-Patent Reference 1 includes such descriptions as "a model incorporating an influence of crosstalk caused by the other eye" and "consideration of an influence of the tissue around the eyeball and so on", but no specific method or mathematical expression is suggested, nor is any approach discussed. In other words, the configuration disclosed by Non-Patent Reference 1 has low accuracy in estimating an electro-oculogram using the electro-oculography model, thus having a problem of low accuracy in gaze detection.

SUMMARY OF THE INVENTION

The present invention is conceived to solve the problem as described above, and it is an object of the present invention to provide an electro-oculography estimating device which formulates, so as to incorporate into a model, influences of an amount of crosstalk between both eyes and tissues in a head region, to thereby calculate an electro-oculogram with high accuracy.

In addition, another object of the present invention is to provide an eye-gaze tracking device which allows detecting a three-dimensional gaze position (gaze point) including a depth direction.

An electro-oculography estimating device according to an aspect of the present invention is an electro-oculography estimating device which estimates an electro-oculography theoretical value that is a theoretical value of an electro-oculogram generated in a living body, and the electro-oculography estimating device includes: a distance obtaining unit which obtains (i) a right-eye corneal distance and a right-eye retinal distance each of which is a distance to an arbitrary three-dimensional spatial position from a corresponding one of a right eye cornea and a right eye retina, and (ii) a left-eye corneal distance and a left-eye retinal distance each of which is a distance to the arbitrary three-dimensional spatial position from a corresponding one of a left eye cornea and a left eye retina; and an electro-oculography theoretical value calculating unit which calculates the theoretical value of the electro-oculogram generated at the arbitrary three-dimensional spatial position, using, as input into an electro-oculography model, the right-eye corneal distance, the right-eye retinal distance, the left-eye corneal distance, and the left-eye retinal distance obtained by the distance obtaining unit, the electro-oculography model being a function for calculating the electro-oculography theoretical value generated at the arbitrary three-dimensional spatial position.

Here, the "arbitrary three-dimensional spatial position" is a surface, interior, or the like of the living body. Although a major object of the present invention aims to calculate the theoretical value of the electro-oculogram generated in the electrodes attached to a skin of the living body, this is not the only object of the present invention.

This electro-oculography estimating device is a model that calculates with high accuracy, as a model representing the "influence of crosstalk caused by the other eye", the theoretical value of the electro-oculogram generated in the arbitrary three-dimensional spatial position, using a function in accordance with a distance from each of the cornea and retina of each eye. In addition, since the electro-oculography estimating device allows calculating the electro-oculogram with high accuracy even in a region where a large amount of crosstalk occurs (near centers of both eyes), a nose-pad portion of the eyeglasses may include an electrode, thus allowing increasing freedom in attachment position of the electrodes. In addition, it is possible to calculate three-dimensional coordinates of the gaze point, and also to perform distance measuring; thus, various applications are expected.

Preferably, based on an assumption that a right eye and a left eye are gazing at a same gaze point, the distance obtaining unit calculates the right-eye corneal distance, the right-eye retinal distance, the left-eye corneal distance, and the left-eye retinal distance, based on a parallel movement component of both eyes, and a depth distance from both of the eyes to the same gaze point or a vergence movement component of both of the eyes.

Normally, identifying horizontal and vertical gaze angles of both eyes requires four electrodes except for a reference electrode (or a ground electrode (for example, the electrode to be provided beside an ear). However, the electro-oculography estimating device according to the aspect of the present invention requires only three electrodes (except for the reference electrode) because the condition which renders the gazes of both eyes cross each other at a point in the three-dimensional space. In addition, the electro-oculography estimating device according to the aspect of the present invention has advantages of reducing circuit scale and calculation amount as well as increasing speed. Note that to "cross each other at a point" is not necessarily precisely crossing at a point but is a concept which includes some errors.

More preferably, the electro-oculography model includes predetermined coefficients each of which is individually settable for a corresponding one of the right-eye corneal distance, the right-eye retinal distance, the left-eye corneal distance, and the left-eye retinal distance.

Here, the "predetermined coefficients" are values each of which corresponds to a charge amount, permittivity, current density, and conductivity, and so on.

In the electro-oculography estimating device, as a specific model of the "consideration of an influence of the tissue around the eyeball and so on", the influences of elements such as bones, muscles, and cells are modeled by assuming the interior of the head region as a non-uniform permittivity space and assuming each of the predetermined coefficients as settable for a corresponding one of the right-eye corneal distance, right-eye retinal distance, left-eye corneal distance, and left-eye retinal distance. This allows calculating the electro-oculogram with high accuracy.

Note that a three-dimensional distribution of the permittivity space may be held in a three-dimensional look-up table or the like after dividing the intra-head model into subregions.

More preferably, in the electro-oculography model, when: $r_1$, $r_2$, $r_3$, and $r_4$ represent, respectively, the right-eye corneal distance, the right-eye retinal distance, the left-eye corneal distance, and the left-eye retinal distance; $f_1$, $f_2$, $f_3$, and $f_4$ represent, respectively, a function for converting the right-eye corneal distance, the right-eye retinal distance, the left-eye corneal distance, and the left-eye retinal distance into the electro-oculogram; and $a_1$, $a_2$, $a_3$, and $a_4$ represent, respectively, the predetermined coefficients each of which is settable for the corresponding one of the right-eye corneal distance, the right-eye retinal distance, the left-eye corneal distance, and the left-eye retinal distance, and when the electro-oculography theoretical value is represented by $$\hat{v}, \quad [\text{Math 2}]$$

$a_1$ and $a_2$ are not zero at the same time, and $a_3$ and $a_4$ are not zero at the same time, in accordance with:

$$\hat{v} = \alpha_1 f_1(r_1) + \alpha_2 f_2(r_2) + \alpha_3 f_3(r_3) + \alpha_4 f_4(r_4). \quad [\text{Math 3}]$$

More preferably, the electro-oculography model is represented by:

$$\hat{v} = \alpha_1/r_1 + \alpha_2/r_2 + \alpha_3/r_3 + \alpha_4/r_4. \quad [\text{Math 4}]$$

In addition, the electro-oculography estimating device described above may further include a model parameter estimating unit which estimates the predetermined coefficients $a_1$, $a_2$, $a_3$, and $a_4$ each of which is obtained for a corresponding one of a plurality of gaze positions so that a difference between a theoretical voltage and an observation voltage is smallest, the theoretical voltage being generated at a corresponding one of a plurality of electrodes provided at different positions and calculated using the electro-oculography model, and the observation voltage being observed at the plurality of electrodes.

Preferably, when, for each of the plurality of electrodes i (i=1, ..., N): $\Delta v_i = (\Delta v_{i,1}, \ldots, \Delta v_{i,M})^t$ represents the observation voltage at a corresponding one of M different gaze positions $\theta_j$ (j=1, ..., M); $a_i = (a_{i,1}, a_{i,2}, a_{i,3}, a_{i,4})^t$ represents the predetermined coefficients each of which is settable for the corresponding one of the right-eye corneal distance, the right-eye retinal distance, the left-eye corneal distance, and the left-eye retinal distance; $r_{i,j,1}$, $r_{i,j,2}$, $r_{i,j,3}$, and $r_{i,j,4}$, represent, respectively, the right-eye corneal distance, the right-eye retinal distance, the left-eye corneal distance, and the left-eye retinal distance; and $f_{i,1}$, $f_{i,2}$, $f_{i,3}$, and $f_{i,4}$ represent, respectively, the function for converting the right-eye corneal distance, the right-eye retinal distance, the left-eye corneal distance, and the left-eye retinal distance, and when a matrix $A_i$ is represented by $$A_i = \begin{pmatrix} f_{i,1}(r_{i,1,1}) & f_{i,2}(r_{i,1,2}) & f_{i,3}(r_{i,1,3}) & f_{i,4}(r_{i,1,4}) \\ \vdots & \vdots & \vdots & \vdots \\ f_{i,1}(r_{i,M,1}) & f_{i,2}(r_{i,M,2}) & f_{i,3}(r_{i,M,3}) & f_{i,4}(r_{i,M,4}) \end{pmatrix} \quad [\text{Math 5}]$$

and when, for a reference electrode R: $a_R = (a_{R,1}, a_{R,2}, a_{R,3}, a_{R,4})^t$ represents the predetermined coefficients each of which is settable for the corresponding one of the right-eye corneal distance, the right-eye retinal distance, the left-eye corneal distance, and the left-eye retinal distance at the corresponding one of the M different gaze positions $\theta_j$ (j=1, ..., M); $r_{R,i,1}$, $r_{R,i,2}$, $r_{R,i,3}$, and $r_{R,i,4}$ represent, respectively, the right-eye corneal distance, the right-eye retinal distance, the left-eye corneal distance, and the left-eye retinal distance; and $f_{R,1}$, $f_{R,2}$, $f_{R,3}$, and $f_{R,4}$ represent, respectively, the function for converting the right-eye corneal distance, the right-eye retinal distance, the left-eye corneal distance, and the left-eye retinal distance, and when a matrix $A_R$ is represented by $$A_R = \begin{pmatrix} f_{R,1}(r_{R,1,1}) & f_{R,2}(r_{R,1,2}) & f_{R,3}(r_{R,1,3}) & f_{R,4}(r_{R,1,4}) \\ \vdots & \vdots & \vdots & \vdots \\ f_{R,1}(r_{R,M,1}) & f_{R,2}(r_{R,M,2}) & f_{R,3}(r_{R,M,3}) & f_{R,4}(r_{R,M,4}) \end{pmatrix}, \quad [\text{Math 6}]$$

the model-parameter estimating unit calculates each of the predetermined coefficients $a_i$ and $a_R$ for the plurality of electrodes and the reference electrode, in accordance with:

$$\alpha_R = -\left(A_R' \left(\sum_{i=1}^{N} B_i\right) A_R\right)^{-1} A_R' \left(\sum_{i=1}^{N} B_i \Delta v_i\right) \quad [\text{Math 7}]$$

$$\alpha_i = (A_i' A_i)^{-1} A_i' (A_R \alpha_R + \Delta v_i)$$

(However, $B_i = A_i (A_i^t A_i)^{-1} A_i^t - I$, where I is a unit matrix).

Here the "reference electrode" is a ground electrode, or the like.

In addition, the model-parameter estimating unit may estimate the predetermined coefficients $a_1$, $a_2$, $a_3$, and $a_4$, using the observation voltage at the plurality of electrodes, the observation voltage being observed during eyeball movement that moves in a front-rear direction with respect to the living body from which the electro-oculogram is to be measured.

In addition, the model-parameter estimating unit may estimate the predetermined coefficients $a_1$, $a_2$, $a_3$, and $a_4$, using the observation voltage at the plurality of electrodes, the observation voltage being obtained by saccadic movement.

In addition, the electro-oculography model may be configured using a look-up table indicating a correspondence relationship between the electro-oculography theoretical value and a gaze direction of a user.

With this, it is possible to realize a nonlinear conversion processing in a small circuit size in the case of a configuration using hardware, and to reduce the calculation amount and achieve high-speed processing in the case of a configuration using software.

In addition, the electro-oculography estimating device described above may further include at least one electrode which is provided between both eyes of a user, measures the electro-oculogram, and outputs an electro-oculography original signal.

For example, when the electrodes are provided in the left and right sides of the face, as a result of vergence movement, the distance at which the left eye cornea is away from the electrode on the right side and the distance at which the right eye cornea is away from the right side are (almost) the same, and likewise, the distance at which the left eye retina is closer to electrode on the left side and the distance at which the right eye retina is closer to the electrode on the right side are (almost) the same. Thus, vergence movement does not generate any electro-oculogram in a differential voltage between these electrodes.

In addition, for example, even in the case of two electrodes provided only on the left side of the face (or only on the right side), when the distance between them are close, the distance at which the cornea is away from each electrode is almost the same, and the distance at which the retina is closer is almost the same as well. Thus, in this case, vergence movement does not generate any electro-oculogram in the differential voltage as a result of vergence movement, either.

Thus, to detect the vergence movement, it is necessary to provide at least one electrode between both eyes.

Preferably, the at least one electrode is incorporated in a frame of eyeglasses, and includes a plurality of electrodes each of which is provided at a position at which the eyeglasses contact skin.

By providing the electrode as a nose pad of the eyeglasses, it is possible to provide the at least one electrode between both eyes without interfering with design aesthetics.

In addition, the electro-oculography estimating device described above may further include a plurality of electrodes each of which is positioned in front and back of an ear, measures the electro-oculogram, and outputs an electro-oculography original signal.

An electro-oculography calculating method according to another aspect of the present invention is an electro-oculography calculating method for calculating, by an electro-oculography calculating device, a theoretical value of an electro-oculogram generated in a living body, and the electro-oculography calculated method includes: obtaining (i) a right-eye corneal distance and a right-eye retinal distance each of which is a distance to an arbitrary three-dimensional spatial position from a corresponding one of a right eye cornea and a right eye retina, and (ii) a left-eye corneal distance and a left-eye retinal distance each of which is a distance to the arbitrary three-dimensional spatial position from a corresponding one of a left eye cornea and a left eye retina; and calculating the theoretical value of the electro-oculogram generated at the arbitrary three-dimensional spatial position, using, as input into an electro-oculography model, the right-eye corneal distance, the right-eye retinal distance, the left-eye corneal distance, and the left-eye retinal distance obtained in the obtaining, the electro-oculography model being a function for calculating the theoretical value of the electro-oculogram generated at the arbitrary three-dimensional spatial position.

An eye-gaze tracking device according to another aspect of the present invention is an eye-gaze tracking device which detects a gaze direction of a user based on an electro-oculogram, and the eye-gaze tracking device includes: an electro-oculography measuring unit which measures the electro-oculogram generated by eyeball movement, and outputs an electro-oculography original signal; a calibration index presenting unit which presents a calibration index to the user; a saccade detecting unit which detects saccadic movement and outputs an electro-oculography change amount that is an amount of change in the electro-oculogram before and after the saccadic movement, the saccadic movement being rapid eyeball movement that occurs when a gaze position of the user moves to the calibration index presented by the calibration index presenting unit; a calibration parameter calculating unit which calculates predetermined coefficients of an electro-oculography model based on a position of the calibration index presented by the calibration index presenting unit and the electro-oculography change amount that is output from the saccade detecting unit, using (i) a right-eye corneal distance and a right-eye retinal distance each of which is a distance to an arbitrary three-dimensional spatial position from a corresponding one of a right-eye cornea and a right-eye retina, (ii) a left-eye corneal distance and a left-eye retinal distance each of which is a distance to the arbitrary three-dimensional spatial position from a corresponding one of a left-eye cornea and a left-eye retina; and (iii) the predetermined coefficients, the electro-oculography model being a function for calculating the theoretical value of the electro-oculogram generated at the arbitrary three-dimensional spatial position, and the predetermined coefficients being individually settable for a corresponding one of the right-eye corneal distance, the right-eye retinal distance, the left-eye corneal distance, and the left-eye retinal distance; and a calibration unit which detects the gaze direction of the user from the electro-oculogram, based on the electro-oculography model.

In this eye-gaze tracking device, even in the case where a crosstalk potential is generated between both eyes, it is possible to individually detect, with high accuracy, the gaze angle of each of the right and the left eyes. In addition, it is also possible to detect the three-dimensional coordinates of the gaze point, thus allowing distance measuring.

Preferably, the saccade detecting unit includes: a delayed signal generating unit which delays the electro-oculography original signal for a predetermined delay time and outputs a delayed signal; a subtraction unit which generates an output signal obtained by subtracting the delayed signal from the electro-oculography original signal; and a saccade determination unit which determines that a signal larger than a predetermined threshold is a saccade signal representing the saccadic movement, the signal being included in the output signal, and the predetermined delay time is shorter than a period of time for which the user is gazing at the calibration index.

A wearable camera according to another aspect of the present invention is a wearable camera which captures an image in a gaze direction of a user, and includes: an imaging unit; the eye-gaze tracking device described above; and an imaging control unit which causes the imaging unit to capture the image in the gaze direction detected by the eye-gaze tracking device.

A head-mounted display according to another aspect of the present invention is a head-mounted display which moves a mouse pointer in a gaze direction of a user, and the head-mounted display includes: a display unit which displays an image and the mouse pointer; the eye-gaze tracking device described above; and a display control unit which moves the mouse pointer in the gaze direction detected by the eye-gaze tracking device, the mouse pointer being displayed on the display unit.

Electronic eyeglasses according to anther aspect of the present invention are electronic eyeglasses which change a focal point of each of lenses according to a gaze position of a user, and the electronic eyeglasses include: lenses each having a changeable focal point; the eye-gaze tracking device described above; and a focus control unit which changes the focal point of each of the lenses according to the gaze position detected by the eye-gaze tracking device.

A program according to another aspect of the present invention is a program for calculating a theoretical value of an electro-oculogram generated in a living body, and the program causes a computer to execute: obtaining (i) a right-eye corneal distance and a right-eye retinal distance each of which is a distance to an arbitrary three-dimensional spatial position from a corresponding one of a right eye cornea and a right eye retina, and (ii) a left-eye corneal distance and a left-eye retinal distance each of which is a distance to the arbitrary three-dimensional spatial position from a corresponding one of a left eye cornea and a left eye retina; and calculating the theoretical value of the electro-oculogram generated at the arbitrary three-dimensional spatial position, using, as input into an electro-oculography model, the right-eye corneal distance, the right-eye retinal distance, the left-eye corneal distance, and the left-eye retinal distance obtained in the obtaining, the electro-oculography model being a function for calculating the theoretical value of the electro-oculogram generated at the arbitrary three-dimensional spatial position.

With the electro-oculography estimating device according to the present invention, it is possible to calculate the electro-oculogram with high accuracy. In addition, according to the eye-gaze tracking device according to the present invention, it is possible to detect a three-dimensional gaze position (gaze point) including a depth direction with high accuracy.

Further Information about Technical Background to This Application

The disclosure of Japanese Patent Application No. 2009-262679 filed on Nov. 18, 2009 including specification, drawings and claims is incorporated herein by reference in its entirety.

BRIEF DESCRIPTION OF THE DRAWINGS

These and other objects, advantages and features of the invention will become apparent from the following description thereof taken in conjunction with the accompanying drawings that illustrate a specific embodiment of the invention. In the Drawings:

FIG. 10 is a diagram showing a table which is an example of calibration parameter and holds more than one combination of an electro-oculography change amount and an eyeball movement angle that correspond to each other.

FIG. 11 is a diagram showing a table which is another example of the calibration parameter and holds more than one combination of an electro-oculography change amount and a gazing position that correspond to each other;

DESCRIPTION OF THE PREFERRED EMBODIMENTS

Hereinafter, embodiments of the present invention will be described with reference to the drawings.

First Embodiment

An eye-gaze tracking device according to a first embodiment of the present invention will be described. First, a configuration of the eye-gaze tracking device according to the present embodiment will be described; then, an electro-oculography model in the present invention will be described; and next, a method of estimating a model parameter will be described. Lastly, an eye-gaze tracking method using the electro-oculography model will be described. Note that the present embodiment, when using an electro-oculogram or the estimated model parameter, is realized as an electro-oculography estimating device which calculates an electro-oculography theoretical value that is a theoretical value of an electro-oculogram generated at a three-dimensional spatial position in a head region, and is realized, when using the electro-oculography theoretical value calculated in gaze detection, as an electro-oculography measuring device which separates the electro-oculogram from an observation voltage; however, the following will describe the eye-gaze tracking device which detects a gaze angle of a user based on the observation voltage.

<1.1 Eye-Gaze Tracking Device>

Figure 1:
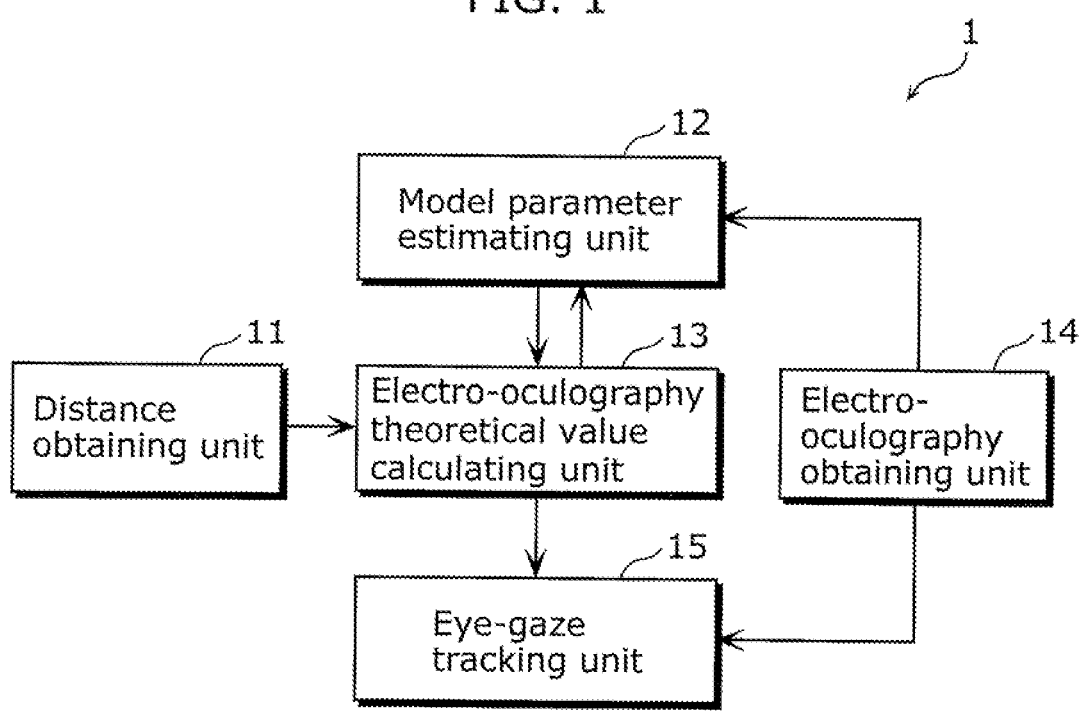
FIG. 1 is a block diagram showing a configuration of an eye-gaze tracking device according to a first embodiment of the present invention.

FIG. 1 is a block diagram showing a configuration of an eye-gaze tracking device according to a first embodiment of the present invention.

An eye-gaze tracking device 1 includes: a distance obtaining unit 11, an electro-oculography theoretical value calculating unit 13, a model-parameter estimating unit 12, an electro-oculography obtaining unit 14, and an eye-gaze tracking unit 15.

The distance obtaining unit 11 obtains: a right-eye corneal distance and a right-eye retinal distance each of which is a distance to an arbitrary three-dimensional spatial position from a corresponding one of a right eye cornea and a right eye retina; and a left-eye corneal distance and a left-eye retinal distance each of which is a distance to the arbitrary three-dimensional spatial position from a corresponding one of a left eye cornea and a left eye retina. Preferably, the distance obtaining unit 11 calculates, by assuming that gaze points of the right and left eyes are identical, the right-eye corneal distance, the right-eye retinal distance, the left-eye corneal distance, and the left-eye retinal distance, based on parallel movement components of both eyes and depth distances from both eyes to the gaze point or vergence movement components of both eyes.

The electro-oculography theoretical value calculating unit 13 calculates the theoretical value of the electro-oculogram generated at the arbitrary three-dimensional spatial position as a result of inputting the right-eye corneal distance, the right-eye retinal distance, the left-eye corneal distance, and the left-eye retinal distance that have been obtained by the distance obtaining unit 11, into the electro-oculography model that is a function for calculating the electro-oculography theoretical value generated at the arbitrary three-dimensional spatial position from the right-eye corneal distance, the right-eye retinal distance, the left-eye corneal distance, and the left-eye retinal distance.

Here, the "arbitrary three-dimensional spatial position" is a surface, an interior of the living body, or the like. Although the object of the present embodiment is to calculate the theoretical value of the electro-oculogram generated in the electrodes attached to a skin of a living body, the object of the present embodiment is not limited to this.

The electro-oculography model includes predetermined coefficients each of which is individually settable for a corresponding one of the right-eye corneal distance, the right-eye retinal distance, the left-eye corneal distance, and the left-eye retinal distance.

In the electro-oculography model, when: $r_1$, $r_2$, $r_3$, and $r_4$ represent, respectively, the right-eye corneal distance, the right-eye retinal distance, the left-eye corneal distance, and the left-eye retinal distance; $f_1$, $f_2$, $f_3$, and $f_4$ represent, respectively, a function for converting the right-eye corneal distance, the right-eye retinal distance, the left-eye corneal distance, and the left-eye retinal distance into an electro-oculogram; and $a_1$, $a_2$, $a_3$, and $a_4$, represent, respectively, the predetermined coefficients each of which is settable for the corresponding one of the right-eye corneal distance, the right-eye retinal distance, the left-eye corneal distance, and the left-eye retinal distance, and when the electro-oculography theoretical value is represented by $$\hat{v},$$ [Math 8]

$$\hat{v} = a_1 f_1(r_1) + a_2 f_2(r_2) + a_3 f_3(r_3) + a_4 f_4(r_4).$$ [Math 9]

Note that $a_1$ and $a_2$ are not zero at the same time. In addition, $a_3$ and $a_4$ are not zero at the same time.

In addition, the electro-oculography model can also be represented by:

$$\hat{v} = \alpha_1/r_1 + \alpha_2/r_2 + \alpha_3/r_3 + \alpha_4/r_4. \quad \text{[Math 10]}$$

The model-parameter estimating unit 12 estimates the predetermined coefficients $a_1$, $a_2$, $a_3$, and $a_4$ that are included in the electro-oculography model and each of which is individually settable for a corresponding one of the right-eye corneal distance, the right-eye retinal distance, the left-eye corneal distance, and the left-eye retinal distance so that, at each of a plurality of gaze positions, a difference between a theoretical voltage that is generated at a corresponding one of the plurality of electrodes provided at different positions and calculated using an electro-oculography model and the observation voltage observed at the plurality of electrodes is smallest. The predetermined coefficient will be described later.

In other words, when, for each of the plurality of electrodes i (i=1, ..., N): $\Delta_{vi} = (\Delta_{vi,1}, \text{to } \Delta_{vi,M})^t$ represents the observation voltage at a corresponding one of M different gaze positions $\theta_j$ (j=1, ..., M); $a_1 = (a_{1,1}, a_{j,2}, a_{i,3}, a_{i,4})^t$ represents the predetermined coefficients each of which is settable for the corresponding one of the right-eye corneal distance, the right-eye retinal distance, the left-eye corneal distance, and the left-eye retinal distance; $r_{i,j,1}, r_{i,j,2}, r_{i,j,3},$ and $r_{i,j,4}$ represent, respectively, the right-eye corneal distance, the right-eye retinal distance, the left-eye corneal distance, and the left-eye retinal distance; and $f_{i,j,1}, f_{i,j,2}, f_{i,j,3},$ and $f_{i,j,4}$ represent, respectively, the function for converting the right-eye corneal distance, the right-eye retinal distance, the left-eye corneal distance, and the left-eye retinal distance, and when a matrix $A_i$ is represented by $$A_i = \begin{pmatrix} f_{i,1}(r_{i,1,1}) & f_{i,2}(r_{i,1,2}) & f_{i,3}(r_{i,1,3}) & f_{i,4}(r_{i,1,4}) \\ \vdots & \vdots & \vdots & \vdots \\ f_{i,1}(r_{i,M,1}) & f_{i,2}(r_{i,M,2}) & f_{i,3}(r_{i,M,3}) & f_{i,4}(r_{i,M,4}) \end{pmatrix} \quad \text{[Math 11]}$$

and when, for a reference electrode R, $a_R = a_{R,1}, a_{R,2}, a_{R,3}, a_{R,4})^t$ represents the predetermined coefficients each of which is settable for the corresponding one of the right-eye corneal distance, the right-eye retinal distance, the left-eye corneal distance, and the left-eye retinal distance at the corresponding one of the M different gaze positions $e_j$ (j=1, ..., M); $r_{R,i,1}, r_{R,i,2}, r_{R,i,3},$ and $r_{R,i,4}$ represent, respectively, the right-eye corneal distance, the right-eye retinal distance, the left-eye corneal distance, and the left-eye retinal distance; and $f_{R,1}, f_{R,2}, f_{R,3},$ and $f_{R,4}$ represent, respectively, the function for converting the right-eye corneal distance, the right-eye retinal distance, the left-eye corneal distance, and the left-eye retinal distance, and when a matrix $A_R$ is represented by $$A_R = \begin{pmatrix} f_{R,1}(r_{R,1,1}) & f_{R,2}(r_{R,1,2}) & f_{R,3}(r_{R,1,3}) & f_{R,4}(r_{R,1,4}) \\ \vdots & \vdots & \vdots & \vdots \\ f_{R,1}(r_{R,M,1}) & f_{R,2}(r_{R,M,2}) & f_{R,3}(r_{R,M,3}) & f_{R,4}(r_{R,M,4}) \end{pmatrix} \quad \text{[Math 12]}$$

the model-parameter estimating unit 12 calculates each of the predetermined coefficients $a_i$ and $a_R$ for each of the plurality of electrodes and the reference electrode in accordance with:

$$\alpha_R = -\left(A_R^t \left(\sum_{i=1}^N B_i\right) A_R\right)^{-1} A_R^t \left(\sum_{i=1}^N B_i \Delta v_i\right) \quad \text{[Math 13]}$$

$$\alpha_i = (A_i^t A_i)^{-1} A_i^t (A_R \alpha_R + \Delta v_i)$$

(However, $B_i = A_i(A_i^t A_i)^{-1} A_i^t - I$, where I is a unit matrix).

The model-parameter estimating unit 12 may estimate the predetermined coefficients $a_1$, $a_2$, $a_3$, and $a_4$ for a living body of which an electro-oculogram is to be measured, using observation voltages observed at the plurality of electrodes during eyeball movement in a front-rear direction.

In addition, the model-parameter estimating unit 12 may estimate the predetermined coefficients $a_1$, $a_2$, $a_3$, and $a_4$, using voltages observed at the plurality of electrodes and obtained by saccadic movement.

The electro-oculography obtaining unit 14 measures the electro-oculogram generated by eyeball movement, and outputs an electro-oculography original signal. The electro-oculography obtaining unit 14 corresponds to an electro-oculography measuring unit as claimed in what is claimed is.

The eye-gaze tracking unit 15 detects the gaze direction of the user from the electro-oculography original signal, based on the electro-oculography model. The eye-gaze tracking unit 15 corresponds to a calibration unit of the claims.

Figure 2:
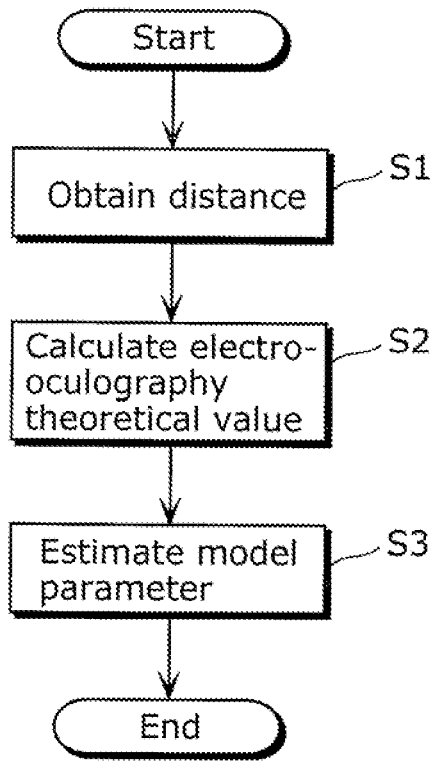
FIG. 2 is a flowchart showing a process in which the eye-gaze tracking device according to the first embodiment estimates a model parameter (predetermined coefficients) of an electro-oculography model.

FIG. 2 is a flowchart showing a process in which the eye-gaze tracking device 1 according to the first embodiment estimates a model parameter (predetermined coefficients) of an electro-oculography model. Here, only the process will be described, and details of each step will be described later.

First, the distance obtaining unit 11 calculates, from the three-dimensional gaze position, a right-eye corneal distance $r_1$, a right-eye retinal distance $r_2$, a left-eye corneal distance $r_3$, and a left-eye retinal distance $r_4$ (S1).

At this time, the electro-oculography theoretical value calculating unit 13 calculates the electro-oculography theoretical value $$\hat{v} \quad \text{[Math 14]}$$

which is generated at the electrodes (S2).

The model-parameter estimating unit 12 calculates a model parameter, based on the electro-oculography theoretical value calculated by the electro-oculography theoretical value calculating unit 13 (S3).

Figure 3:
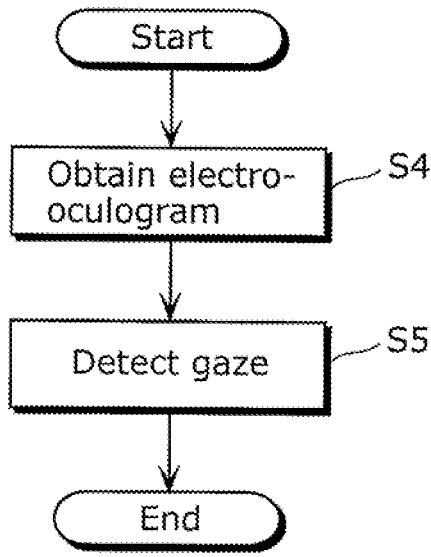
FIG. 3 is a flowchart showing a process in which the eye-gaze tracking device according to the first embodiment detects a gaze.

FIG. 3 is a flowchart showing a process in which the eye-gaze tracking device 1 according to the first embodiment detects a gaze. Here, only the process will be described, and details of each step will be described later.

The electro-oculography obtaining unit 14 measures and obtains the electro-oculogram generated by eyeball movement (S4).

The eye-gaze tracking unit 15 detects the gaze of the user based on the electro-oculogram obtained by the electro-oculography obtaining unit 14 (S5).

<1. 2 Electro-Oculography Model>

Figure 4:
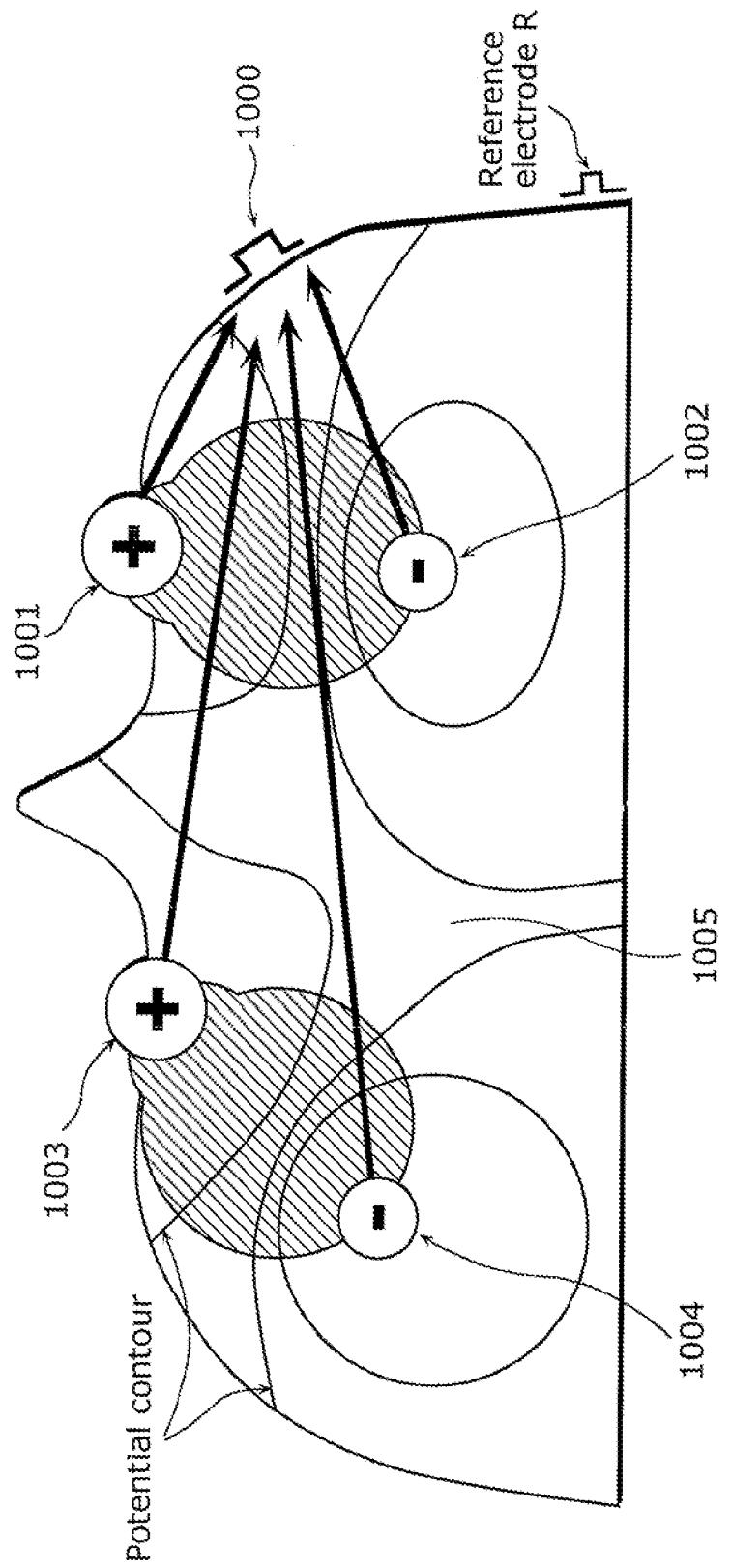
FIG. 4 is a schematic diagram showing an electro-oculography model according to the first embodiment of the present invention.

FIG. 4 is a schematic diagram showing an electro-oculography model according to the first embodiment of the present invention (a cross-sectional view of the head region as viewed from eye position). The electro-oculography model is used for calculating the electro-oculography theoretical value, using the electro-oculography theoretical value calculating unit 13 in the eye-gaze tracking device 1.

The electro-oculography model is a model for representing an influence of elements such as bones, muscles, and cells within the head region as a permittivity space 1005 that is not uniform, and calculating a theoretical value of an observed potential (electro-oculography theoretical value) generated, in an electrode 1000, due to a right-eye corneal charge 1001, a right-eye retinal charge 1002, a left-eye corneal charge 1003, and a left-eye retinal charge 1004.

According to this electro-oculography model, it is possible to calculate an electro-oculography theoretical value with high accuracy not only for one eye but also including a crosstalk potential from the other eye, thus allowing calculating the electro-oculography theoretical value with high accuracy. In addition, at an electrode position where a large amount of crosstalk occurs (near a binocular center), it is also possible to calculate generated potential with high accuracy, thus allowing freedom in attachment position of the electrodes as well as allowing attachment of electrodes at positions appropriate for intended use. Furthermore, the electro-oculography model considers an influence of non-uniform permittivity (or conductivity) due to the bones, muscles, cells within the head region, and so on, it is possible to calculate the electro-oculography theoretical value with higher accuracy.

Hereinafter, the processing for calculating an observed electro-oculography theoretical value v for a three-dimensional gaze position $\theta$ will be described (S1 and S2 in FIG. 2).

Figure 5:
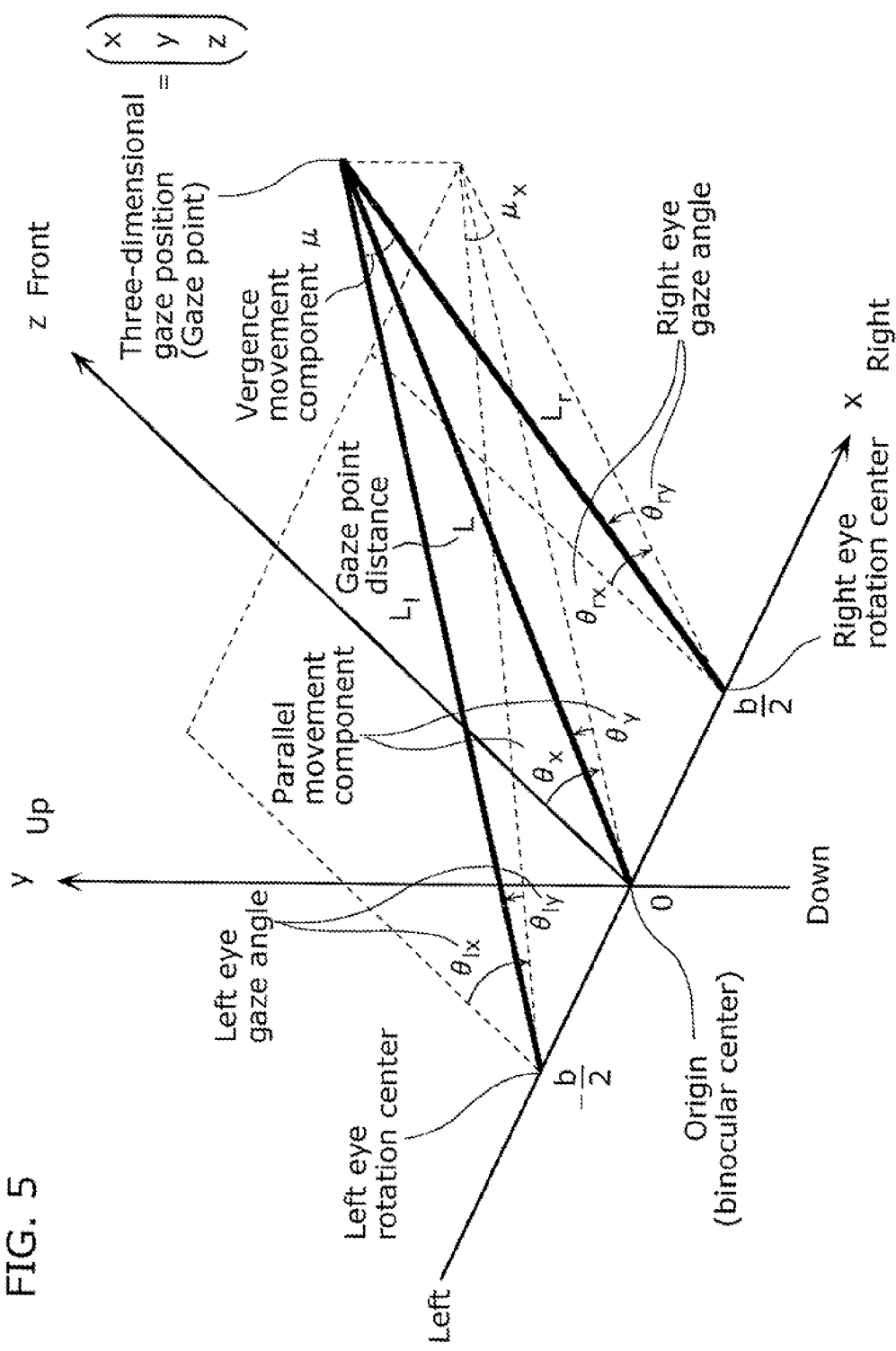
FIG. 5 is an explanatory diagram of each parameter according to the first embodiment of the present invention.

As shown in FIG. 5, it is assumed that a midpoint of a rotation center of each of the right and left eyes (binocular center point) is an origin, with an x-axis representing a rightward direction, a y-axis representing an upward direction, and a z-axis representing a forward direction. Furthermore, it is assumed that: b represents a binocular space; $\theta=(x, y, z)$ represents a three-dimensional gaze position (gaze point); $(\theta_x, \theta_y)$ represents a parallel movement component of both eyes; $\mu$ represents a vergence movement component of both eyes; $(\theta_{rx}, \theta_{ry})$ represents a right-eye horizontal and vertical gaze angle; $(\theta_{lx}, \theta_{ly})$ represents a left-eye horizontal and vertical gaze angle; and L represents a gaze point distance. In addition, it is assumed that a represents an eyeball radius, and $(x_e, y_e, z_e)$ represents electrode coordinates.

Here, $\theta_x$ of the parallel movement component of both eyes $(\theta_x, \theta_y)$ represents degrees of an angle at which both eyes have moved in the x-axis direction from a state of looking frontward, and $\theta_y$ represents degrees of an angle at which both eyes have moved in the y-axis direction from a state of looking frontward. In other words, as shown in FIG. 5, $\theta_x$ represents an angle between the z-axis and a projection line that is a straight line connecting the binocular center point and the gaze point and projected onto an x-y plane (a plane formed by the x-axis and y-axis). In addition, $\theta_y$ represents an angle between the projection line and a straight line connecting the binocular center point and the gaze point.

The vergence movement component $\mu$ is a component to define an angle between the gazes of both eyes when both eyes are looking inward at the same time. In other words, as shown in FIG. 5, $\mu$ represents an angle between a straight line connecting a left-eye rotation center and the gaze point, and a straight line connecting a right-eye rotation center and the gaze point.

Of the right-eye horizontal and vertical gaze angles $(\theta_{rx}, \theta_{ry})$, the horizontal gaze angle $\theta_{rx}$ represents degrees of an angle at which the right eye has moved in the x-axis direction from a state of looking frontward, and $\theta_{ry}$ represents degrees of an angle at which the right eye has moved in the y-axis direction from a state of looking frontward. In other words, as shown in FIG. 5, the horizontal gaze angle $\theta_{rx}$ represents an angle between the z-axis and a projection line that is a line connecting the right-eye rotation center and the gaze point and projected onto the x-y plane. In addition, $\theta_{ry}$ represents an angle between the projection line and a straight line connecting the right-eye rotation center and the gaze point.

Of the left-eye horizontal and vertical gaze angles $(\theta_{lx}, \theta_{ly})$, the horizontal gaze angle $\theta_{lx}$ represents degrees of an angle at which the left eye has moved in the x-axis direction from a state of looking frontward, and $\theta_{ly}$ represents degrees of an angle at which the left eye has moved in the y-axis direction from a state of looking frontward. In other words, as shown in FIG. 5, the horizontal gaze angle $\theta_{lx}$ represents an angle between the z-axis and a projection line that is a line connecting the left-eye rotation center and the gaze point and projected onto the x-y plane. In addition, $\theta_{ly}$ represents an angle between the projection line and a straight line connecting the left-eye rotation center and the gaze point.

There are various types of methods for representing the three-dimensional gaze position $\theta=(x, y, z)$; however, in the following description, the three dimensional gaze position is represented as $\theta=(\theta_x, \theta_y, z)$, using the parallel movement components of both eyes and the z-coordinates of the three-dimensional gaze position (gaze point). Note that, for another method, the three-dimensional gaze position may also be represented as $\theta=(\theta_x, \theta_y, \mu)$, using the vergence movement component $\mu$ of both eyes. Note that according to the present embodiment, both eyes are assumed as gazing at the same gaze point.

First, the distance obtaining unit 11 calculates the horizontal and vertical gaze angle $(\theta_{rx}, \theta_{ry}, \theta_{lx}, \theta_{ly})$ in accordance with (Expression 2) below (S1 in FIG. 2).

[Math 15]

$$\theta_{rx} = \tan^{-1}(\tan\theta_x - b/2z)$$

$$\theta_{lx} = \tan^{-1}(\tan\theta_x + b/2z)$$

$$\theta_{ry} = \tan^{-1}(\tan\theta_y \cos\theta_{rx}/\cos\theta_x)$$

$$\theta_{ly} = \tan^{-1}(\tan\theta_y \cos\theta_{lx}/\cos\theta_x) \quad \text{(Expression 2)}$$

Next, the distance obtaining unit 11 calculates, in accordance with (Expression 3) below, the right-eye corneal distance $r_1$, the right-eye retinal distance $r_2$, the left-eye corneal distance $r_3$, and the left-eye retinal distance $r_4$ each of which represents a distance from each electrode to a corresponding one of the right eye cornea, the right eye retina, the left eye cornea, and the left eye retina (S1 in FIG. 2).

[Math 16]

$$r_1 = \sqrt{\begin{aligned}&(x_e - b/2 - a\cos\theta_{ly}\sin\theta_{lx})^2 + \\&(y_e - a\sin\theta_{ly})^2 + (z_e - a\cos\theta_{ly}\cos\theta_{lx})^2\end{aligned}}$$

$$r_2 = \sqrt{\begin{aligned}&(x_e - b/2 + a\cos\theta_{ly}\sin\theta_{lx})^2 + \\&(y_e + a\sin\theta_{ly})^2 + (z_e + a\cos\theta_{ly}\cos\theta_{lx})^2\end{aligned}}$$

$$r_3 = \sqrt{\begin{aligned}&(x_e + b/2 - a\cos\theta_{ly}\sin\theta_{lx})^2 + \\&(y_e - a\sin\theta_{ly})^2 + (z_e - a\cos\theta_{ly}\cos\theta_{lx})^2\end{aligned}}$$

$$r_4 = \sqrt{\begin{aligned}&(x_e + b/2 + a\cos\theta_{ly}\sin\theta_{lx})^2 + \\&(y_e + a\sin\theta_{ly})^2 + (z_e + a\cos\theta_{ly}\cos\theta_{lx})^2\end{aligned}}$$

(Expression 3)

In addition, permittivity from the electrode to each of the right eye cornea, the right eye retina, the left eye cornea, and the left eye retina is defined as $\epsilon_1, \epsilon_2, \epsilon_3,$ and $\epsilon_4$, respectively, and a charge amount of each of the right eye cornea, the right eye retina, the left eye cornea, and the left eye retina is defined as $q_1, q_2, q_3,$ and $q_4$, respectively. At this time, the electro-oculography theoretical value calculating unit 13 calculates an electro-oculography theoretical value $$\hat{v} \quad \text{[Math 17]}$$

in accordance with (Expression 4) below (S2 in FIG. 2).

[Math 18]

$$\hat{v} = \frac{q_1}{4\pi\varepsilon_1 r_1} + \frac{q_2}{4\pi\varepsilon_2 r_2} + \frac{q_3}{4\pi\varepsilon_3 r_3} + \frac{q_4}{4\pi\varepsilon_4 r_4} \quad \text{(Expression 4)}$$

Figure 6:
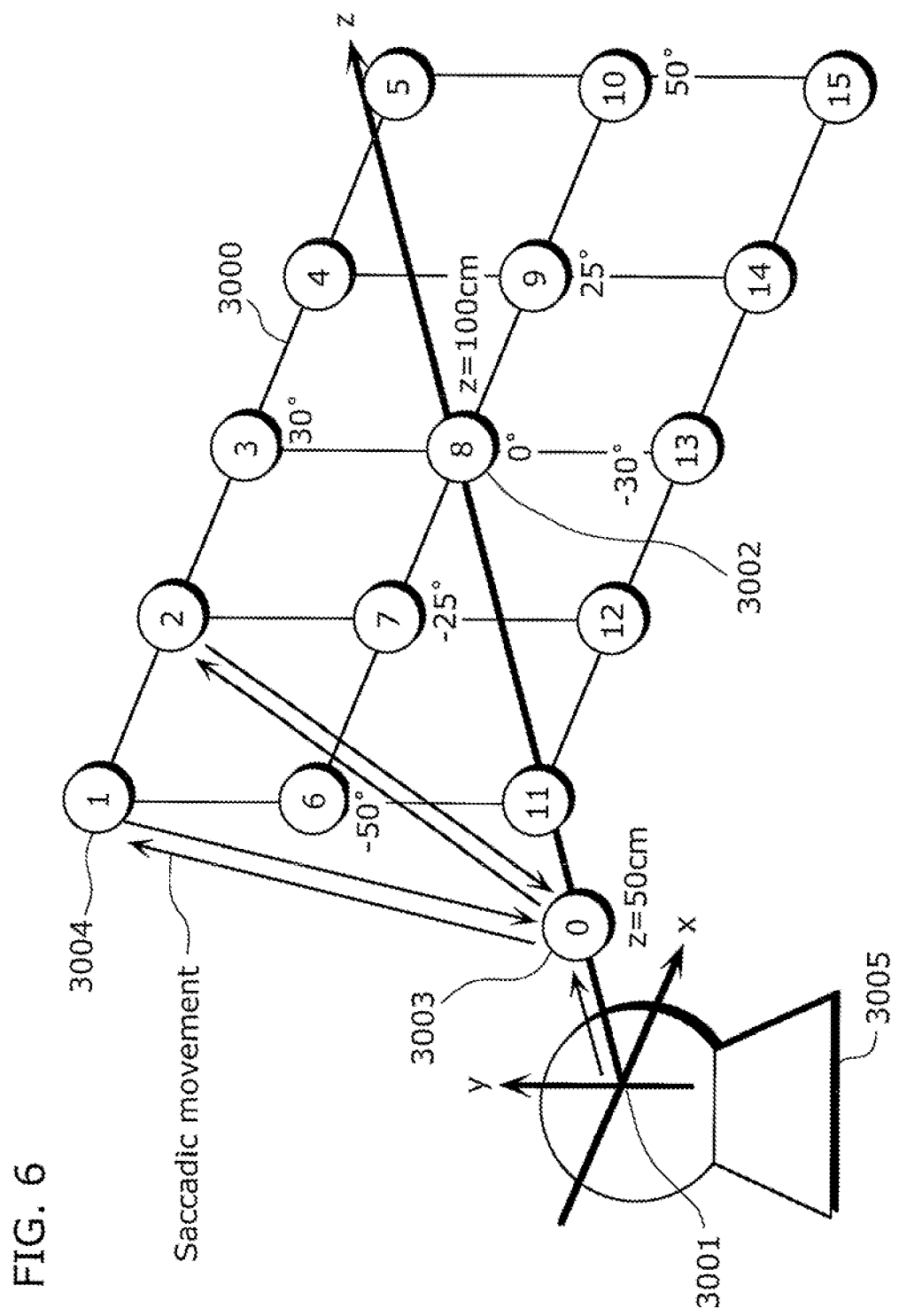
FIG. 6 is an explanatory diagram of a calibration method according to the first embodiment of the present invention.

Note that here, the electro-oculography theoretical value is calculated based on infinity as a reference potential; however, since the processing is easier when assuming, as the reference potential, the potential observed when the user is gazing at the reference index ($\theta_x = \theta_y = 0$, $z = $ a predetermined value) that is shown in FIG. 6, it is preferable to subtract the electro-oculogram at this time as an offset potential. However, the following will omit the description of the offset potential for simplicity of description.

Here, furthermore, assuming that values representing the charge amount and permittivity do not vary depending on eyeball movement, (Expression 4) is simplified as (Expression 5), using the predetermined coefficients $a_1$, $a_2$, $a_3$, and $a_4$.

[Math 19]

$$\hat{v} = a_1/r_1 + a_2/r_2 + a_3/r_3 + a_4/r_4 \quad \text{(Expression 5)}$$

Note that here, for simplicity of description, infinity is assumed as a reference voltage (0 V), but the electro-oculography theoretical value calculating unit 13 may calculate and subtract the offset potential observed when the user is gazing frontward because the electro-oculogram when gazing at the front ($\theta_x = \theta_y = 0$) is assumed as the reference voltage.

<1. 3 Estimating Model Parameter (Calibration)>

The following will describe calibration of unknown parameters (model parameters) of the electro-oculography model, that is: eyeball radius a, binocular space b, electrode coordinates ($x_e$, $y_e$, $z_e$), and the predetermined coefficients $a_1$, $a_2$, $a_3$, and $a_4$. This calibration processing is performed by the model-parameter estimating unit 12 (S3 in FIG. 2). Note that in the following description, assuming that the eyeball radius a and the binocular space b as a=12 mm and b=65 mm, respectively, the model-parameter estimating unit 12 estimates only the electrode coordinates ($x_e$, $y_e$, $z_e$), and the predetermined coefficients $a_1$, $a_2$, $a_3$, and $a_4$.

<1.3. 1 Obtaining Calibration Data>

First, the electro-oculography obtaining unit 14 obtains calibration data (learning data). A method of obtaining the calibration data will be described with reference to FIG. 6. Note that the following will describe highly accurate calibration using saccadic movement (saccadic eye movement) by reducing mixing of drift noise (low-frequency noise) that is generated in calibration. However, only an outline of the processing is described here, and a method for presenting a calibration index and a method for detecting saccadic movement will be described in detail in the second embodiment.

(Preparation)

A user is seated with a binocular center 3001 pointed at a center point 3002 of a monitor 3000, and gazes at a reference index 3003 (on the z-axis) provided between the user and the monitor 3000. The reference index 3003 may be anything such as substituting the user's thumb that is stood in front of the eyes, but should preferably be something that does not move.

(Obtaining Data)

(1) When a calibration index 3004 is presented on the monitor 3000 (gaze position θ), the user gazes at the calibration index 3004 through saccadic movement (saccadic eye movement). At this time, the electro-oculography obtaining unit 14 detects the observation voltage change amount Δv as a result of the saccadic movement (amount of change in the voltage observed at the electrode when the user is gazing at the reference index 3003 and when the user is gazing at the calibration index 3004, and records calibration data (θ, Δv).

(2) When the calibration index 3004 disappears, the user gazes at the reference index 3003 again.

(3) (1) and (2) are repeated up to No. 1 to No. 15 of the calibration index 3004 (provided in a matrix of three rows and five columns, at intervals of 25° horizontally, and 15° vertically).

(4) Furthermore, the electro-oculography obtaining unit 14 obtains calibration data at a plurality of positions z (for example, z=20 cm, 50 cm, z=100 cm, . . . ), by moving the position of the monitor 3000, or moving the position of the user 3005, and so on.

This allows obtaining a plurality of data pairs (learning data and calibration data) of (θ, Δv), including a z-direction (depth direction). In addition, since the calibration data is obtained using (high-speed) saccadic movement, it is possible to prevent drift noise (low frequency noise) from being mixed into the calibration data, thus allowing highly accurate calibration.

<1.3.2 Model Parameter Estimation>

Next, the model-parameter estimating unit 12 estimates model parameter based on the calibration data obtained by the electro-oculography obtaining unit 14. Specifically, the model-parameter estimating unit 12 estimates, in accordance with an electro-oculography model (Expression 5), an electro-oculography theoretical value $$\Delta\hat{v}_{i,j} \quad \text{[Math 20]}$$

which corresponds to M pieces of calibration data ($\theta_i$, $\Delta v_{i,j}$)(j=1, . . . , M), each of which corresponds to each electrode i (i=1, . . . , N). The model-parameter estimating unit 12 calculates a model parameter such that a sum of squared errors (cost function J) between the calculated electro-oculography theoretical value $$\Delta\hat{v}_{i,j} \quad \text{[Math 21]}$$

and the measured electro-oculogram $\Delta v_{i,j}$ is smallest, as shown in (Expression 6) below:

[Math 22]

$$J = \sum_{i=1}^{N} \sum_{j=1}^{M} (\Delta v_{i,j} - \Delta\hat{v}_{i,j})^2 \quad \text{(Expression 6)}$$

At this time, the model-parameter estimating unit 12 (1) optimizes, of the electro-oculography model (Expression 5), the electrode coordinates ($x_e$, $y_e$, $z_e$) that are a parameter of a nonlinear term (reciprocal term of each of $r_1$, $r_2$, $r_3$, and $r_4$), by performing a search; and (2) calculates an optimum value of a linear parameter (predetermined coefficients) $a_1$, $a_2$, $a_3$, and $a_4$ in accordance with a mathematical expression, using the least square method. The following will describe this in detail.

(1) First, the model-parameter estimating unit 12 sets an initial value of the electrode coordinates ($x_e$, $y_e$, $z_e$). In the case of not performing a search for the electrode coordinates, it is necessary to accurately measure the electrode coordinates in advance; whereas, in the case of performing the search, rough visual coordinates are provided as an initial value.

(2) Next, the model-parameter estimating unit 12 derives a least squares solution of the predetermined coefficients $a_1$, $a_2$, $a_3$, and $a_4$ at the set electrode coordinates.

First, an electro-oculography theoretical value corresponding to M pieces of calibration data, which is

[Math 23]
$$\hat{v}(j=1 \sim M)$$

is represented in a matrix in accordance with (Expression 7) below.

[Math 24]
$$\begin{pmatrix} \hat{v}_1 \\ M \\ \hat{v}_M \end{pmatrix} = \begin{pmatrix} 1/r_{1,1} & 1/r_{1,2} & 1/r_{1,3} & 1/r_{1,4} \\ \vdots & \vdots & \vdots & \vdots \\ 1/r_{M,1} & 1/r_{M,2} & 1/r_{M,3} & 1/r_{M,4} \end{pmatrix} \begin{pmatrix} \alpha_1 \\ \alpha_2 \\ \alpha_3 \\ \alpha_4 \end{pmatrix} \quad \text{(Expression 7)}$$

$$\Leftrightarrow \hat{v} = A\alpha$$

Here, $r_{j,1}$, $r_{j,2}$, $r_{j,3}$, and $r_{j,4}$ represent, respectively, the right-eye corneal distance, the right-eye retinal distance, the left-eye corneal distance, and the left-eye retinal distance at the time of measuring a j-th calibration data. Since all the parameters regarding the matrix A including electrode coordinates and the other parameters are set, the matrix A is a constant matrix.

This is prepared for each electrode i (i=1, . . . , N). That is, all the electro-oculography theoretical values are represented by (Expression 8) below:

[Math 25]
$$\hat{v}_i = A_i \alpha_i \quad \text{(Expression 8)}$$

Here, a potential of each electrode is a potential for the reference electrode (or ground electrode). Thus, the distance obtaining unit 11 and the electro-oculography theoretical value calculating unit 13 calculates an electro-oculography theoretical value of a reference electrode R shown in (Expression 9) below in the same manner.

[Math 26]
$$\hat{v}_R = A_R \alpha_R \quad \text{(Expression 9)}$$

With this, the model-parameter estimating unit 12 calculates, in accordance with (Expression 10) below, a potential

[Math 27]
$$\Delta \hat{v}_{i,j}$$

which is a potential corresponding to the potential generated at each electrode and corresponding to the reference electrode in accordance with:

[Math 28]
$$\Delta \hat{v}_{i,j} = v_{i,j} - v_{R,j} \quad \text{(Expression 10)}$$

so as to calculate $a_i$ (i=1, . . . , N) and $a_R$ such that the cost function J as shown in (Expression 11) below is smallest:

[Math 29]
$$J = \sum_{i=1}^{N} \sum_{j=1}^{M} (\Delta v_{i,j} - (v_{i,j} - v_{R,j}))^2 \quad \text{(Expression 11)}$$

That is, by solving (Expression 12) below to express the solution in a matrix, it is possible to obtain a normal equation as shown in (Expression 13) below:

[Math 30]
$$\frac{\partial J}{\partial \alpha_i} = 0, \quad \frac{\partial J}{\partial \alpha_R} = 0 \quad \text{(Expression 12)}$$

[Math 31]
$$A_i^t(A_i \alpha_i - A_R \alpha_R - \Delta v_i) = 0 \quad \text{(Expression 13)}$$
$$A_R^t \left( \sum_{i=1}^{N} A_i \alpha - N A_R \alpha_R - \sum_{i=1}^{N} \Delta v_i \right) = 0$$

When solving this normal equation, it is possible to obtain (Expression 14) below:

[Math 32]
$$\alpha_R = -\left( A_R^t \left( \sum_{i=1}^{N} B_i \right) A_R \right)^{-1} A_R^t \left( \sum_{i=1}^{N} B_i \Delta v_i \right) \quad \text{(Expression 14)}$$
$$\alpha_i = (A_i^t A_i)^{-1} A_i^t (A_R \alpha_R + \Delta v_i)$$

(However, $B_i = A_i(A_i^t A_i)^{-1} A_i^t - I$, where I is a unit matrix).

In other words, the model-parameter estimating unit 12 can obtain the least squares solution of the cost function J (Expression 11), by calculating the predetermined coefficients $a_R$ and $a_i$ in accordance with (Expression 14). Note that other than the method of directly solving the normal equation, the least squares solution of the cost function J (Expression 11) may be calculated using a house holder QR decomposition method and so on.

The model-parameter estimating unit 12 searches for the electrode coordinates ($x_e$, $y_e$, $z_e$) using a nonlinear optimization technique (gradient descent method, Levenberg-Marquardt method, and so on), by repeating the processing (1) and (2) described above until the cost function J (Expression 11) falls within a predetermined error range. In addition, the model-parameter estimating unit 12 may set an electrode search range and search for all the electrode coordinates based on a predetermined granularity. For example, since a displacement of the electrode often falls within a maximum range of 5 cm or less, the electrode coordinates may be searched for at intervals of 5 mm, based on a search range of ±5 cm in each of the x-, y-, and z-directions with respect to the initial value (visual measurement position of the electrode).

As described above, the model parameter estimating method optimizes a nonlinear parameter (the electrode coordinates) by search, and calculates an optimal value of a linear parameter (the predetermined coefficients) in accordance with mathematical expressions. This allows highly-accurate high-speed estimation of an optimum model parameter. In addition, normally, the electro-oculogram is generated in front and back of the ear, and even in the ear. This method has advantages of allowing, by further considering the electro-oculogram generated at the reference electrode (or ground electrode), highly-accurate estimation and freedom in attachment position of the reference electrode.

Note that attachment of the reference electrode to a position at which no electro-oculogram is generated (earlobe, and so on) simplifies the formula for calculating the least squares solution described above, thus allowing reducing an amount of calculation and circuit size. In addition, by assuming all the predetermined coefficients $a_1$, $a_2$, $a_3$, and $a_4$ as an identical value, it is possible to calculate, despite decrease in model accuracy, the optimum value with high speed by simple calculation.

<1.4 Gaze Detection>

Lastly, an eye-gaze tracking method will be described. The eye-gaze tracking processing based on this method is performed by the electro-oculography obtaining unit 14 and the eye-gaze tracking unit 15.

The electro-oculography obtaining unit 14 obtains an electro-oculogram (observation voltage) of the user (S4 in FIG. 3).

The eye-gaze tracking unit 15 searches for a gaze vector 8 such that a square error of the theoretical voltage in accordance with the electro-oculography model is the smallest. That is, the eye-gaze tracking unit 15 calculates the gaze vector 8 such that a sigma term is smallest (S5 in FIG. 3).

[Math 33]

$$\theta = \underset{\theta}{\operatorname{argmin}} \sum_{i=1}^{N} (\Delta v_i - \Delta \hat{v}_i)^2 \quad \text{(Expression 15)}$$

At this time, it is preferable to previously hold, in a three-dimensional look-up table, a theoretical voltage at each gaze position ($\theta = (\theta_x, \theta_y, z)$), which is $$\Delta \hat{v}_i \quad \text{[Math 34]}$$

because this allows reducing circuit scale or amount of calculation. In other words, with reference to the three-dimensional look-up table, it is possible to uniquely derive, from the observed voltage, the three-dimensional gaze position corresponding to the observed voltage. Note that, in consideration of the case where gazes of both eyes do not cross each other at a point, the gaze position may be four-dimensionally represented as ($\theta_{rx}, \theta_{ry}, \theta_{lx}, \theta_{ly}$) and may be held in a four-dimensional look-up table.

Note that the method of calculating the gaze vector B is not limited to the least square method (Expression 15), but any method that minimizes the error between the observed value and the theoretical value may be used, such as methods using another evaluation function (high-order statistics, entropy, and so on), and techniques such as the Kalman filter or the Monte Carlo filter.

Note that a relationship between each parameter shown in FIG. 5 is as follows:

[Math 35]

$$\tan\theta_{lx} = \tan\theta_x + \frac{b}{z}, \tan\theta_{rx} = \tan\theta_x - \frac{b}{z},$$

$$\tan\theta_{ly} = \tan\theta_y \left(\frac{\cos\theta_{lx}}{\cos\theta_x}\right), \tan\theta_{ry} = \tan\theta_y \left(\frac{\cos\theta_{rx}}{\cos\theta_x}\right)$$

$$z = \frac{2b}{\tan\theta_{lx} - \tan\theta_{rx}} = y\left(\frac{\cos\theta_{lx}}{\tan\theta_{ly}}\right) =$$

$$y\left(\frac{\cos\theta_x}{\tan\theta_y}\right) = y\left(\frac{\cos\theta_{rx}}{\tan\theta_{ry}}\right), x = z\tan\theta_x, y =$$

$$z\left(\frac{\tan\theta_y}{\cos\theta_x}\right)$$

$$L = \frac{z}{\cos\theta_x \cos\theta_y}, L_l = \frac{z}{\cos\theta_{lx} \cos\theta_{ly}}, L_r = \frac{z}{\cos\theta_{rx} \cos\theta_{ry}}$$

$$\theta_{lx} = \theta_x + \frac{\mu_x}{2}, \theta_{rx} = \theta_x - \frac{\mu_x}{2}, \cos\mu = \frac{L_l^2 + L_r^2 - 4b^2}{2 L_l L_r}$$

By using this relationship to detect, for example, a gaze point distance L, it is possible to apply the eye-gaze tracking method to an application which executes processing in accordance with the distance.

Figure 7:
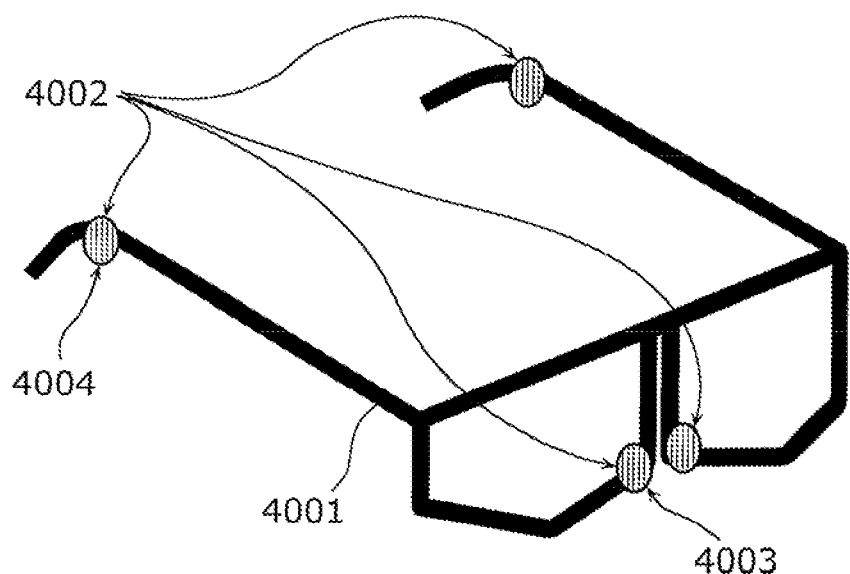
FIG. 7 is a schematic diagram of an example electrode layout in an eyeglass-type configuration according to the first embodiment of the present invention.
Figure 8:
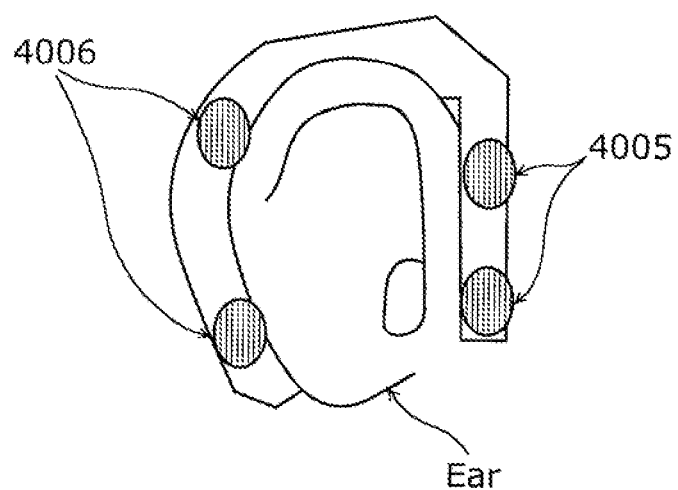
FIG. 8 is a schematic diagram of an example electrode layout in an on-ear configuration according to the first embodiment of the present invention.

Note that in the case of attaching a plurality of electrodes, the electrodes may be attached in the z-direction with spaces. This allows increasing amplitude in response to the vergence movement, and increases recognition accuracy in the z-direction. As shown in FIG. 7, it the case of incorporating an electrode 4002 into eyeglasses 4001, it is preferable to incorporate the electrode 4002 at a nose-pad position 4003 and a frame-ear contact position 4004. In addition, as shown in FIG. 8, in the case of incorporating the electrode 4002 into an on-ear part, electrodes 4005 and 4006 may be provided in front and rear portions of the ear.

Thus far, the eye-gaze tracking device 1 according to the first embodiment of the present invention allows detecting, at an arbitrary electrode attachment position, a highly-accurate three-dimensional gaze position using a smaller number of electrodes (at least three electrodes), in accordance with an electro-oculography model which considers influences of an amount of crosstalk between both eyes, the tissue around the eyeballs, and so on.

Second Embodiment

Next, the above-described calibration method using saccadic movement (hereinafter, also referred to as the calibration method) will be described in detail. First, an overall configuration will be described, and then two types of saccade detecting methods will be described. In addition, a countermeasure method for deterioration in calibration accuracy caused by blinking will be described. Note that each configuration described below may be combined in an arbitrary combination as long as such a combination does not diminish the advantageous effect to be produced by the present invention.

In addition, the following will describe not an electro-oculography model but a calibration method using a linear model and a linear parameter a as shown in (Expression 16), but the method may likewise be applied to the electro-oculography model.

<2.1 Overall Configuration>

Figure 9:
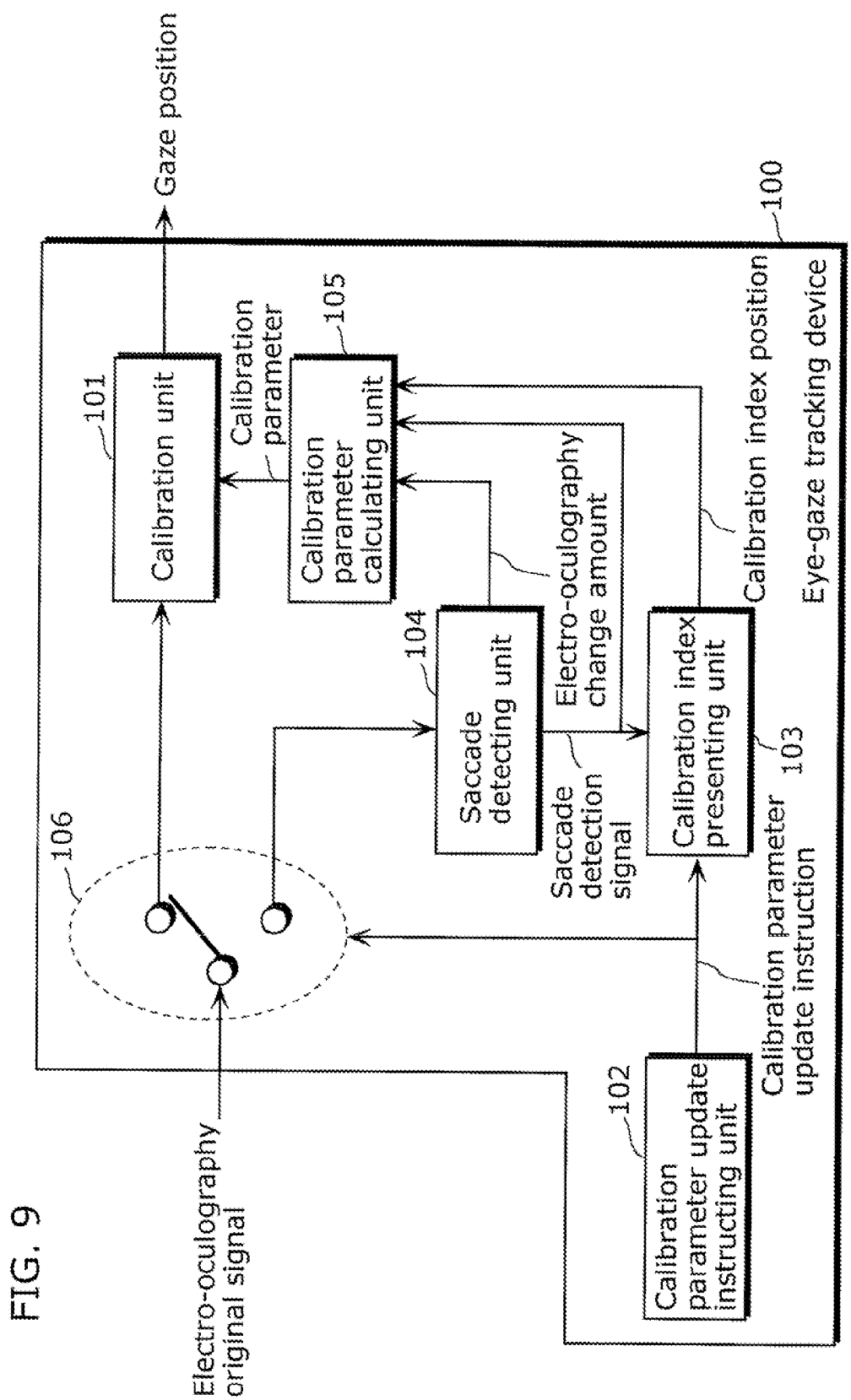
FIG. 9 is a block diagram showing a configuration of an eye-gaze tracking device according to a second embodiment of the present invention.

FIG. 9 is a block diagram showing a configuration of an eye-gaze tracking device 100 according to a second embodiment of the present invention. The eye-gaze tracking device 100 shown in FIG. 9 includes: a calibration unit 101, a calibration parameter update instructing unit 102, and a calibration index presenting unit 103, and a saccade detecting unit 104, a calibration parameter calculating unit 105, and a switch 106.

The calibration unit 101 measures an electro-oculogram at electrodes attached around the user's eyes, and converts the electro-oculography original signal that is output from the electro-oculography measuring unit (not shown in the figure) into a gaze position (which can also be read, hereafter, as "gaze direction").

The calibration parameter update instructing unit 102 instructs to update a calibration parameter.

The calibration index presenting unit 103 presents a calibration index in response to the instruction to update a calibration parameter update instruction.

The saccade detecting unit 104 detects a saccade signal from the electro-oculography original signal, and outputs an electro-oculography change amount that is an amount of change in electro-oculogram before and after the detected saccadic movement.

The calibration parameter calculating unit 105 calculates a calibration parameter based on the electro-oculography change amount that is output from the saccade detecting unit 104 and the position of the calibration index that is output from the calibration index presenting unit 103.

The switch 106 switches a destination to which the electro-oculography original signal is output, to one of the calibration unit 101 and the saccade detecting unit 104.

The electro-oculography measuring unit is typically an electrode to be attached around the user's eye. The attachment method is not restricted to a specific method; however, for example, electrodes to be attached to a tail or a head of the eye may be used in combination. Alternatively, the electrodes may be attached to one of upper or lower sides of the eye, or may be attached to both sides. Furthermore, the electrodes may be attached to upper and lower sides of the temple.

The calibration unit 101 calculates the user's gaze position from the electro-oculography original signal, using the calibration parameter that is previously held. Here, the calibration parameter is a parameter for converting the electro-oculography original signal into an eyeball movement angle, and a calibration coefficient a used in (Expression 16) below can be given as an example of such calibration parameter.

Generally, it is known that a measurement electro-oculogram $V_{a-b}$ linearly changes as long as the eyeball movement angle θ is within a certain range. In other words, it is possible to calculate the measurement electro-oculogram $V_{a-b}$ in accordance with (Expression 16) below, using the calibration coefficient a and the eyeball movement angle θ.

[Math 36]

$$V_{a-b} = a \times \theta \quad \text{(Expression 16)}$$

An example of operation in calibration using the EOG method will be described. When the electro-oculogram Ve as the electro-oculography original signal is input into the calibration unit 101, the calibration unit 101 calculates the eyeball movement angle θ using (Expression 16). In addition, the calibration unit 101 calculates the gaze position from the movement angle θ, using a distance between the user and the gazed object, and so on. According to the procedure above, the calibration unit 101 can calculate the gaze position from the electro-oculogram. Note that a distance measuring sensor, for example, may be used although the method of measuring the distance between the user and the gazed object is not particularly restricted.

Note that the present embodiment is not limited to the calibration method using (Expression 16), and may use, as a calibration parameter, a table which holds, as shown in FIG. 10, a plurality of combinations of the electro-oculography change amount and the eyeball movement angle that correspond each other. Furthermore, a table holding, as shown in FIG. 11, a plurality of combinations of the electro-oculogram, display coordinates, camera coordinates, and so on that correspond to each other may also be used as a calibration parameter.

In the case of occurrence of an event such as a start of the gaze detection, the calibration parameter update instructing unit 102 outputs a calibration parameter update instruction signal to the calibration index presenting unit 103 and the switch 106. Then, the calibration parameter update instructing unit 102 stops the output of the calibration parameter update instruction signal when terminating the update of the calibration parameter.

The switch 106 switches, in accordance with the calibration parameter update instruction, the destination of the electro-oculography original signal to one of the calibration unit 101 and the saccade detecting unit 104.

The saccade detecting unit 104 detects a saccade signal from the electro-oculography original signal, and calculates, using the detected saccade signal, an amount of change in electro-oculogram at the time of occurrence of the saccade. A saccade (saccadic eye movement) is eyeball movement caused to capture an object, which is projected on a peripheral retina having low resolution, with a central retinal fovea having high resolution, and it is known that the speed of the movement is very high at 100 to 500 (°/sec).

Figure 12:
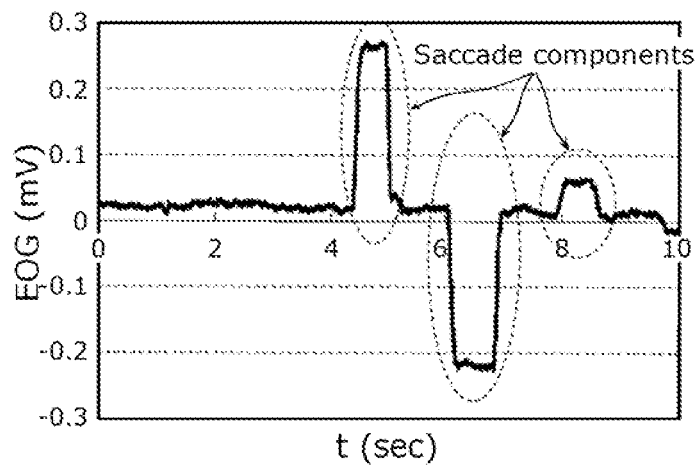
FIG. 12 is a diagram showing an example of an electro-oculography signal including a saccade signal.

FIG. 12 shows an example of a waveform of the electro-oculography signal including a saccade signal. In FIG. 12, each portion enclosed by a dotted line indicates a saccade. When a saccade occurs, after a rapid change occurs in potential, the saccade stops for a certain period of time (fixation), and the potential returns to an initial potential level. This is an example case of moving an eyeball from an index A to another index B by saccade, and moving, again, the eyeball from the index B to the index A by saccade. Generally, a human being obtains information from surroundings, by repeating fixation for approximately 0.3 seconds and a saccade for several dozens of milliseconds.

As one of the methods of detecting a saccade signal from the electro-oculography original signal as shown in FIG. 12, there is a method of applying each of the maximum value filtering and the minimum value filtering on the electro-oculography original signal to calculate the difference. The processing will be described later in detail.

Figure 13:
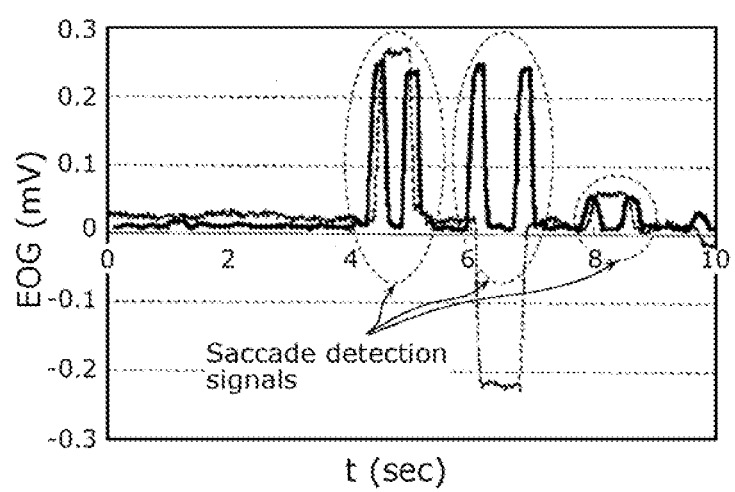
FIG. 13 is a diagram describing a saccade detection signal extracted from the electro-oculography signal in FIG. 12.

FIG. 13 shows an output signal obtained by applying the maximum value filtering and the minimum value filtering on the electro-oculography original signal shown in FIG. 12. As shown in FIG. 13, the output signal includes a peak only when the saccade occurs.

The saccade detecting unit 104 further includes a saccade determination unit (not shown in the figure) that determines a signal that exceeds a predetermined threshold among the output signals, as a saccade signal that indicates a saccadic movement. Then, the saccade detecting unit 104 calculates a change amount of a saccade signal (in other words, an amount of change in the electro-oculogram before or after the saccadic movement) and outputs the calculated change amount to the calibration parameter calculating unit 105. Then, the saccade detecting unit 104 outputs a saccade detection signal indicating that the saccade signal has been detected, to the calibration index presenting unit 103 and calibration parameter calculating unit 105.

Note that, although the minimum value filter and the maximum value filter are used as methods of detecting the saccade signal in the second embodiment, any technique, such as a high-pass filter and the like, may be used as long as it detects a saccade. In addition, although the amount of change in the electro-oculogram that has changed during the saccade is obtained in the second embodiment, the amplitude of the saccade detection signal may also be used.

The calibration index presenting unit 103 presents a calibration index when the calibration parameter update instruction is received. Then, the calibration index presenting unit 103 changes the position to present the calibration index according to the saccade detection signal from the saccade detecting unit 104.

Figure 14:
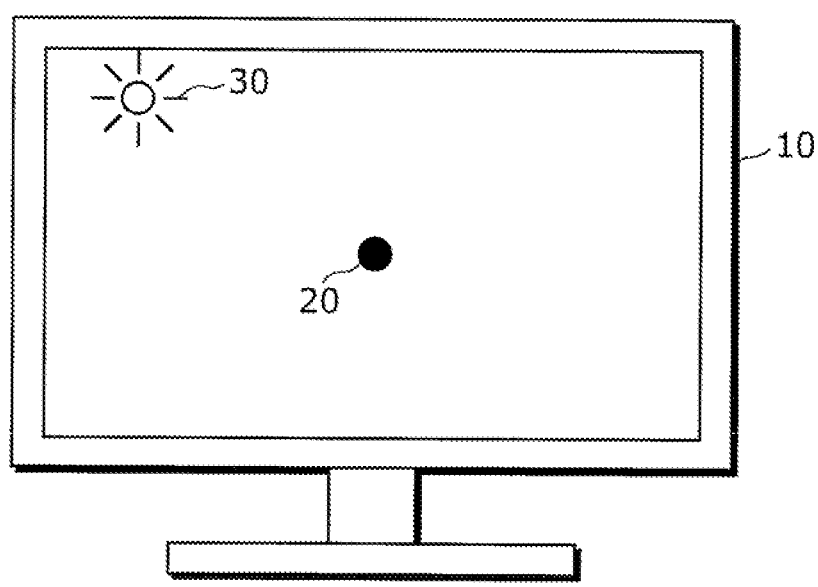
FIG. 14 is a diagram showing a state in which a display shows a calibration index.

In the case where a display 10 as shown in FIG. 14 is used to perform calibration, for example, the calibration index presenting unit 103 causes the first calibration index 20 to be displayed at the center of the display 10 in response to receiving the calibration parameter update instruction. Then, the calibration index presenting unit 103, when receiving a saccade detection signal, causes the second calibration index 30 to be displayed in the upper left. Then, the calibration index presenting unit 103, when receiving a saccade detection signal again, causes the next calibration index to be displayed in the upper right and the like. As described above, it is possible to induce a saccade for a user by changing the position of the calibration index according to the saccade of the user. As described above, the position of the calibration index which is changed according to the saccade of the user is output to the calibration parameter calculating unit 105.

Note that, although in the second embodiment, the first and second calibration indexes 20 and 30 are displayed on the display 10, the method of presenting the calibration index is not limited to this. For example, the calibration index may be displayed on a real space by using a laser pointer and the like. In addition, a calibration index may be selected from among objects (a human face and the like, for example) which exist in the surroundings, by using a camera and so on to output audio information so that a user can recognize the calibration index. Thus, the calibration index presenting unit 103 may be anything as long as it provides output information that allows a user to identify the calibration index.

The calibration parameter calculating unit 105, when receiving the saccade detection signal from the saccade detecting unit 104, updates a calibration parameter using the electro-oculography change amount and the calibration index position. A calculation example of a calibration coefficient a that is one of calibration parameters will be described. First, the calibration parameter calculating unit 105 calculates an eyeball movement angle θ of a user when viewing the calibration index, using a calibration index position and distance information between the user and the object on which the calibration index is displayed (typically, a display), and the like. Then, the calibration coefficient a can be obtained by substituting the electro-oculography change amount Vc and the eyeball movement angle θ which have been input, into (Expression 16). Note that, the method of obtaining the distance information between the user and the display is not specifically limited. For example, a distance measuring sensor or the like may be used, or the calibration parameter update instruction may be output after having a user stand at a position predetermined distance away from the display.

Figure 15:
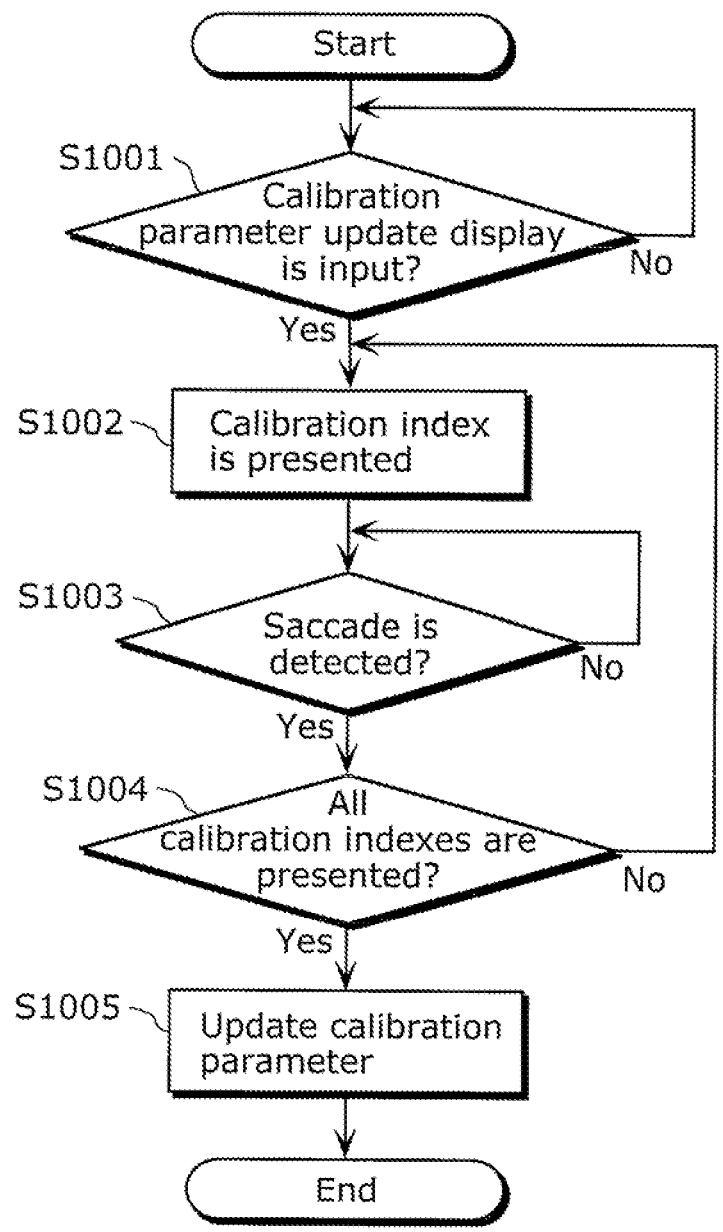
FIG. 15 is a flowchart showing an operation of an eye-gaze tracking device according to the second embodiment of the present invention.

Next, the procedure of updating the calibration parameter performed by the eye-gaze tracking apparatus 100 according to the second embodiment will be described with reference to FIG. 15. The eye-gaze tracking apparatus 100 calculates a new calibration parameter when triggered by an input of a calibration parameter update instruction from outside.

First, the eye-gaze tracking apparatus 100 monitors an input of the calibration parameter update instruction (S1001). The calibration parameter update instruction is transmitted from the calibration parameter update instructing unit 102 to the calibration index presenting unit 103 and the switch 106. The method of inputting the calibration parameter update instruction is not specifically limited. For example, the calibration parameter update instructing unit 102 may receive an instruction from a user or automatically issue the instruction with a predetermined timing such as when turning on the power of the eye-gaze tracking apparatus 100.

Next, the calibration index presenting unit 103 which has received the calibration parameter update instruction (Yes in S1001) presents the first calibration index 20 to the user (S1002). In addition, the calibration index presenting unit 103 notifies the calibration parameter calculating unit 105 of position information of the first calibration index 20. Likewise, the switch 106 which has received the calibration parameter update instruction switches the output of the electro-oculography original signal from the calibration unit 101 to the saccade detecting unit 104.

Next, the saccade detecting unit 104 monitors the electro-oculography original signal that is input via the switch 106 to see whether or not a saccade signal is included (S1003). When the first calibration index 20 is displayed on the display 10, the gaze-path of the user moves from an arbitrary position to the first calibration index 20. At this time, a saccade signal appears.

Note that, the method of detecting a saccade signal is not specifically limited. The method includes, for example, detecting by using a maximum value filter, a minimum value filter, a delay device, and so on. The details of the method will be described later. When a saccade signal is detected (Yes in S1003), the saccade detecting unit 104 outputs a saccade detection signal to the calibration index presenting unit 103. Likewise, the saccade detecting unit 104 outputs the saccade detection signal and the electro-oculography change amount $V_{a-b}$ to the calibration parameter calculating unit 105.

Next, the calibration index presenting unit 103 which has received the saccade detection signal determines whether or not all calibration indexes have been presented to the user (S1004). The number of calibration indexes to be presented may be specified in advance, or the user may be asked whether or not to continue presenting the calibration indexes. Note that the description of the second embodiment assumes the number of calibration indexes that are to be presented as two.

At this point, only the first calibration index 20 is presented (No in S1004), and thus the calibration index presenting unit 103 presents the next calibration index (S1002). Specifically, the first calibration index 20 is deleted from the display 10 and the second calibration index 30 is displayed on the display 10. In addition, the calibration index presenting unit 103 notifies the calibration parameter calculating unit 105 of the position information of the second calibration index 30.

Next, the saccade detecting unit 104 monitors whether or not the electro-oculography original signal includes a saccade signal (S1003). When the second calibration index 30 is displayed on the display 10, the gaze-path of the user moves from the first calibration index 20 to the second calibration index 30. At this time, a saccade signal appears.

The saccade detecting unit 104 which has detected the saccade signal outputs the saccade detection signal and the electro-oculography change amount $V_{a-b}$ in the same manner as the previous time. In addition, in the Step S1004, after the second calibration index 30 is presented, the calibration index presenting unit 103 determines that all of the calibration indexes have been presented (Yes in S1004).

Next, the calibration parameter calculating unit 105 calculates a new calibration parameter based on the position information of the first and second calibration indexes 20 and 30 received from the calibration index presenting unit 103 and the electro-oculography change amount $V_{a-b}$ after the output of the second calibration index 30, which has been received from the saccade detecting unit 104 (S1005). Specifically, an eyeball movement angle θ is calculated using the position information of the first and second calibration indexes 20 and 30. Then, the electro-oculography change amount $V_{a-b}$ and the eyeball movement angle θ are substituted into (Expression 16) to obtain a calibration coefficient a.

Note that in the second embodiment, the method of calculating the calibration coefficient a is described as an example of updating a calibration parameter. However, the method of updating the calibration parameter is not limited to this. For example, it is also possible to use the electro-oculography change amount, the eyeball movement angle, or the calibration index position which have been input into the calibration parameter calculating unit 105 to update a table which holds a plurality of combinations of the electro-oculography change amount, and a corresponding eyeball movement angle or a gaze-path position as shown in FIGS. 10 and 11. In this case, the number of records of the tables in FIGS. 10 and 11 is increased by increasing the total number of the calibration indexes to be presented, thus allowing obtaining a more reliable calibration parameter.

According to the configuration of the second embodiment as described above, the saccade signal is detected from the electro-oculography original signal, and the calibration parameter is updated using the amount of change in the electro-oculogram which has occurred during saccadic movement. As a result, it is possible to correctly calculate the calibration parameter without being affected by a drift which is the problem of the conventional methods.

In addition, it is possible to update a calibration parameter while inducing a saccade of a user. As a result, the user has only to follow a calibration index with his eyes, thus allowing reducing the burden of the user at the time of calibration.

In addition, it is possible to reduce calibration time by holding the calibration parameter as a table as shown in FIGS. 11 and 10.

In addition, it is possible to reduce memory by holding the calibration parameter as a slope of function (calibration coefficient a) of the electro-oculography change amount $V_{a-b}$ and the eyeball movement angle θ.

Note that the saccade detecting unit 104 may detect the saccade signal by applying the high-pass filter. Note that the saccade signal is widely used for detecting eyeball movement or a state of a user, not only in the eye-gaze tracking device 100 described above but also in the fields such as medical equipment, driver supporting devices, user interfaces, and the like. Thus, it is significantly effective to detect a saccade signal with ease and high accuracy.

In addition, it is possible to use the electro-oculography model shown in (Expression 5), instead of (Expression 16). In this case, the calibration parameter calculating unit 105 calculates the predetermined coefficients $a_1$, $a_2$, $a_3$, and $a_4$ in accordance with the model parameter shown in the first embodiment.

<2.2.1 Method of Detecting Saccade 1 (MIN/MAX Filter)>

Figure 16:
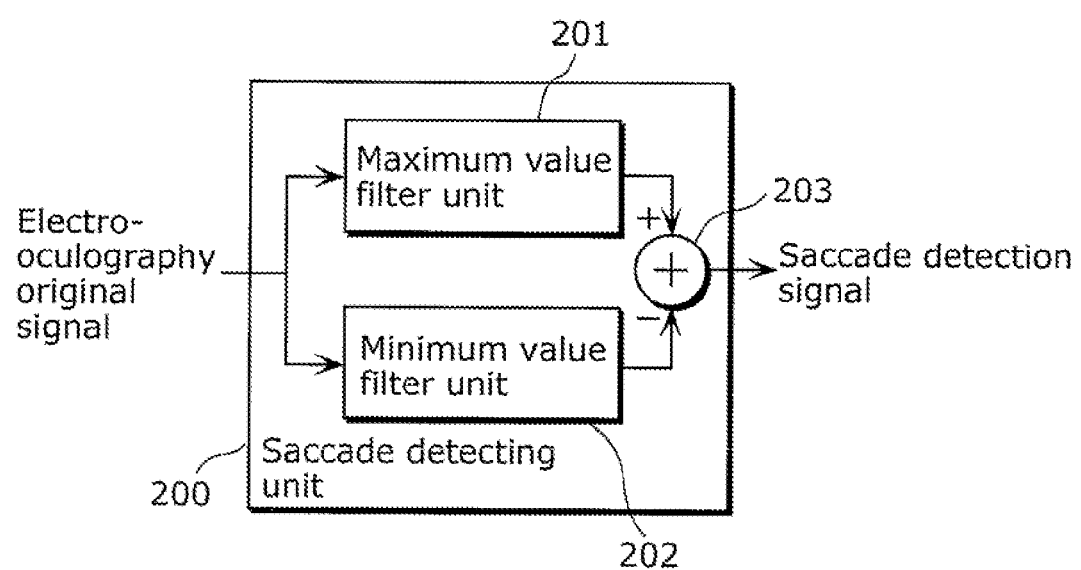
FIG. 16 is a block diagram of a first example of a saccade detecting unit according to the second embodiment of the present invention.

FIG. 16 is a block diagram showing a configuration of a saccade detecting unit 200 according to the second embodiment of the present invention. The saccade detecting unit 200 shown in FIG. 16 includes: a maximum value filter unit (the first filtering unit) 201 which performs maximum value filtering on an electro-oculography original signal; a minimum value filter unit (the second filtering unit) 202 which performs minimum value filtering on the electro-oculography original signal; and a subtraction unit 203.

More specifically, the maximum value filter unit 201 and the minimum value filter unit 202 are connected in parallel to each other. The maximum value filter unit 201 performs the maximum value filtering on the electro-oculography original signal and outputs the first electro-oculography signal. The minimum value filter unit 202 performs the minimum value filtering on the electro-oculography original signal and outputs the second electro-oculography signal. Then, the subtraction unit 203 subtracts the second electro-oculography signal from the first electro-oculography signal to generate an output signal.

Note that the present invention is intended for the case where the electro-oculography original signal does not include a blink component of a user as seen in attaching the electrodes to the right and left of an eyeball or in the measuring method in which the electrodes are attached at a position away from the eye, and the detection of a saccade signal by using such a measuring method will be described.

Next, processing of the maximum value filter unit 201 as shown in FIG. 16 will be described. The maximum value filter unit 201 performs filtering on the electro-oculography original signal f(x) as below.

$$fmax(x)=\max(fmax(x),f(x+i))$$

when $n$ is an odd number, $(-n/2 < i < n/2)$ when $n$ is an even number, $(-n/2 \leq i < n/2)$ or $(-n/2 < i \leq n/2)$ Here, fmax (x) is an electro-oculography signal after the maximum value filtering is performed, n is the number of filter taps, and i is an integer. In addition, max (a, b) is a function that returns a larger value of a and b. Thus, in the maximum value filtering, a sampled value is output which has the largest amplitude in n samples centering on an arbitrary sample f(x) among the electro-oculography original signals. It is possible to obtain a first electro-oculography signal by performing the processing on each of the samples of the electro-oculography original signals.

Figure 17:
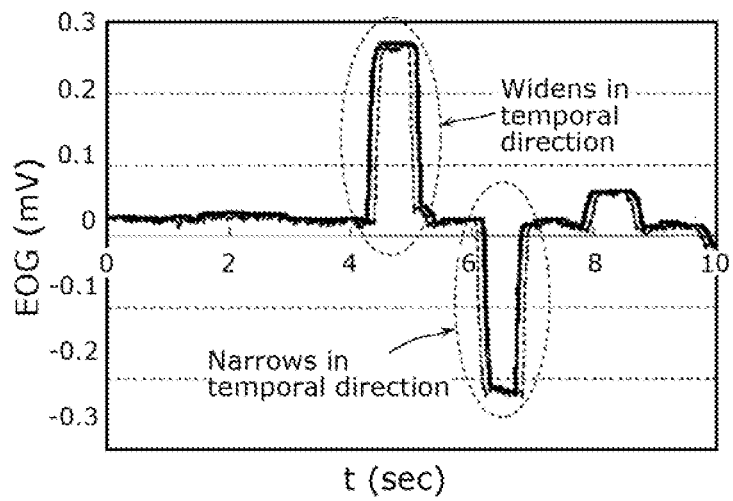
FIG. 17 is a diagram showing an electro-oculography signal obtained by applying maximum value filtering (unit processing period=0.25 minutes) to the electro-oculography signal in FIG. 12.

FIG. 17 shows an example of performing the above-described filtering on the electro-oculography original signal in FIG. 12. Note that a unit processing period for the maximum value filtering is set to 0.25 seconds to detect the saccade signal from the electro-oculography original signal. Note that the unit processing period indicates a time interval including a sample on which a single maximum value filtering is to be performed. In addition, the number of filter taps n of the maximum value filter unit 201 is the number of samples included in the unit processing period (0.25 seconds). Thus, it is possible to calculate the number of filter taps n, using the unit processing period and a sampling frequency for performing A/D conversion on the electro-oculography original signal.

Figure 18:
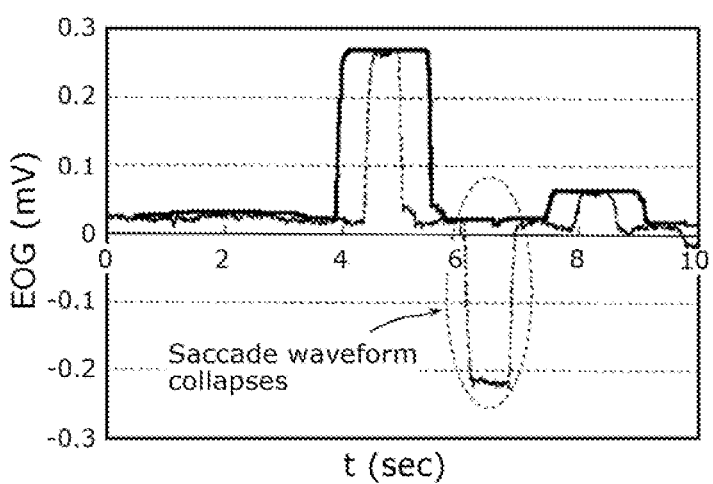
FIG. 18 is a diagram showing an electro-oculography signal obtained by applying maximum value filtering (unit processing period 1.0 minute) to the electro-oculography signal in FIG. 12.

As shown in FIG. 17, when the maximum value filtering is performed on the electro-oculography original signal, a plus signal widens in a temporal direction and a minus signal narrows in the temporal direction. However, when the unit processing period of the maximum value filter unit 201 becomes larger than a general fixation time (approximately 0.3 to 0.4 seconds), a saccade waveform in the minus direction collapses as shown in FIG. 18. FIG. 18 is an example of the maximum value filtering performed with the unit processing period set to 1.0 second. As shown in FIG. 18, since the saccade signal cannot be detected when the saccade waveform collapses, it is necessary to make the unit processing period of the maximum value filter unit 201 shorter than the general fixation time.

Note that, although an example where the unit processing period of the maximum value filtering is 0.25 seconds has been described in the second embodiment, the unit processing period may be any value as long as it is shorter than the general single fixation time.

Next, processing of the minimum value filter unit 202 will be described. The minimum value filter unit 202 performs filtering on the electro-oculography original signal f(x) as described below.

$$fmin(x)=\min(fmin(x),f(x+i))$$

when $n$ is an odd number, $(-n/2 < i < n/2)$ when $n$ is an even number, $(-n/2 \leq i < n/2)$ or $(-n/2 < i \leq n/2)$ Here, fmin (x) is an electro-oculography signal after the minimum value filtering is performed, n is the number of filter taps, and i is an integer. In addition, min (a, b) is a function that returns a larger value of a and b. Thus, in the minimum value filtering, a sampled value is output which has the smallest amplitude in n samples centering on an arbitrary sample f(x) among the electro-oculography original signals. It is possible to obtain a second electro-oculography signal by performing the processing on each of the samples of the electro-oculography original signals.

Figure 19:
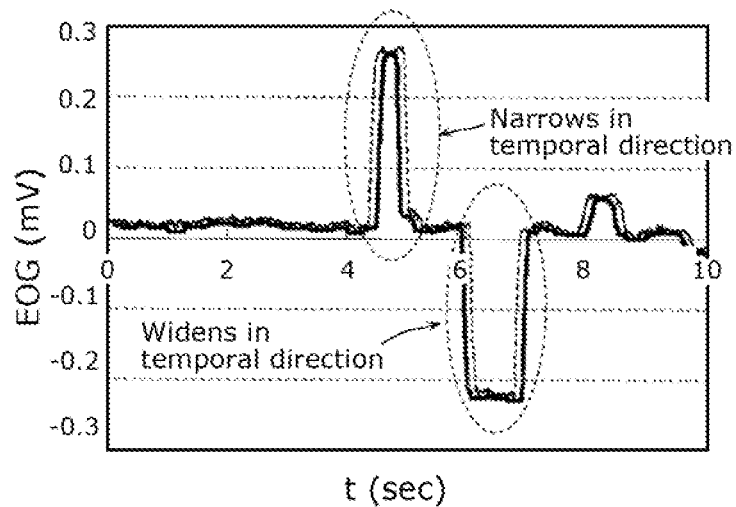
FIG. 19 is a diagram showing an electro-oculography signal obtained by applying minimum value filtering (unit processing period=0.25 minutes) to the electro-oculography signal in FIG. 12.

FIG. 19 shows an example of performing the above-described filtering on the electro-oculography original signal of FIG. 12.

In FIG. 19, the unit processing period for the minimum value filtering is set to 0.25 seconds to detect the saccade signal from the electro-oculography original signal.

Figure 20:
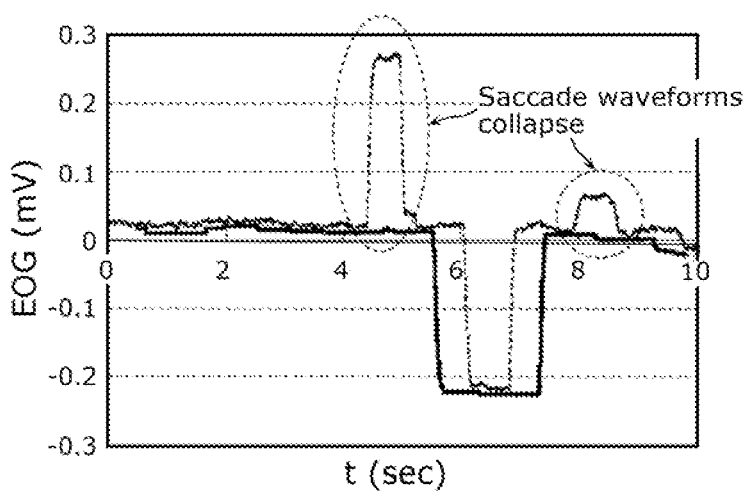
FIG. 20 is a diagram showing an electro-oculography signal obtained by applying minimum value filtering (unit processing period=1.0 minute) to the electro-oculography signal in FIG. 12.

As shown in FIG. 19, when the minimum value filtering is performed on the electro-oculography original signal, a plus signal narrows in the temporal direction and a minus signal widens in the temporal direction. Here, when the unit processing period of the minimum value filter unit 202 becomes larger than a general single fixation time, the saccade waveform in the plus direction collapses as shown in FIG. 20. FIG. 20 is an example of the minimum value filtering performed with the unit processing period set to 1.0 second. Since a saccade component cannot be detected when the saccade waveform collapses as shown in FIG. 20, it is necessary to make the unit processing period of the minimum value filter unit 202 shorter than the general fixation time.

Note that, although an example where the unit processing period of the minimum value filter unit is 0.25 seconds has been described in the second embodiment, the unit processing period may be any value as long as it is shorter than the general single fixation time.

Next, the processing of the subtraction unit 203 will be described. The subtraction unit 203 subtracts the second electro-oculography signal fmin (x) that is output from the minimum value filter unit 202, from the first electro-oculography signal fmax (x) that is output from the maximum value filter unit 201, to thereby extract the saccade signal.

FIG. 13 shows a signal indicating a difference between the first electro-oculography signal shown in FIG. 17 and the second electro-oculography signal shown in FIG. 19. With reference to FIG. 13, it is shown that the detection signal including a period when a saccade occurred is obtained.

The saccade detecting unit 200 generates a saccade detection signal and an electro-oculography change amount based on an output signal as shown in FIG. 13, to output the saccade detection signal and the electro-oculography change amount to the calibration index presenting unit 103 and the calibration parameter calculating unit 105.

For example, when the amount of change in sampled values within a period of time corresponding to a period of time required for saccadic movement exceeds a predetermined threshold, it is determined that a saccadic movement has occurred, so that a saccade detection signal is output. In addition, the amount of change in sampled values is output as an electro-oculography change amount.

Note that, although the maximum value filter unit 201 and the minimum value filter unit 202 are used in the second embodiment, a filter that selects a value close to the maximum value or the minimum value may be used. In this case, it is preferable to select a value that is approximately 90% of the maximum value or the minimum value.

In addition, although the second embodiment has shown an example where the unit processing periods (the numbers of filter taps) of the maximum value filter unit 201 and the minimum value filter unit 202 are set to the same value, different values may be set.

According to the configuration of the second embodiment as described above, a saccade signal is detected by performing each of the maximum value filtering and the minimum value filtering on the electro-oculography original signal and subtracting the second electro-oculography signal on which the minimum value filtering has been performed, from the first electro-oculography signal on which the maximum value filtering has been performed.

Note that other than this, there are methods of subtracting the electro-oculography original signal from the signal on which the maximum value filtering has been performed, and of subtracting the signal on which the minimum value filtering has been performed from the electro-oculography original signal. Although in performing these methods, in some cases, the time at which the saccade signal is detected is more or less ahead or behind the time at which the saccade actually occurred, this does not cause a serious problem when calibration is intended.

As described above, it is possible to easily obtain a saccade signal that includes the time at which a saccade occurred.

Figure 21:
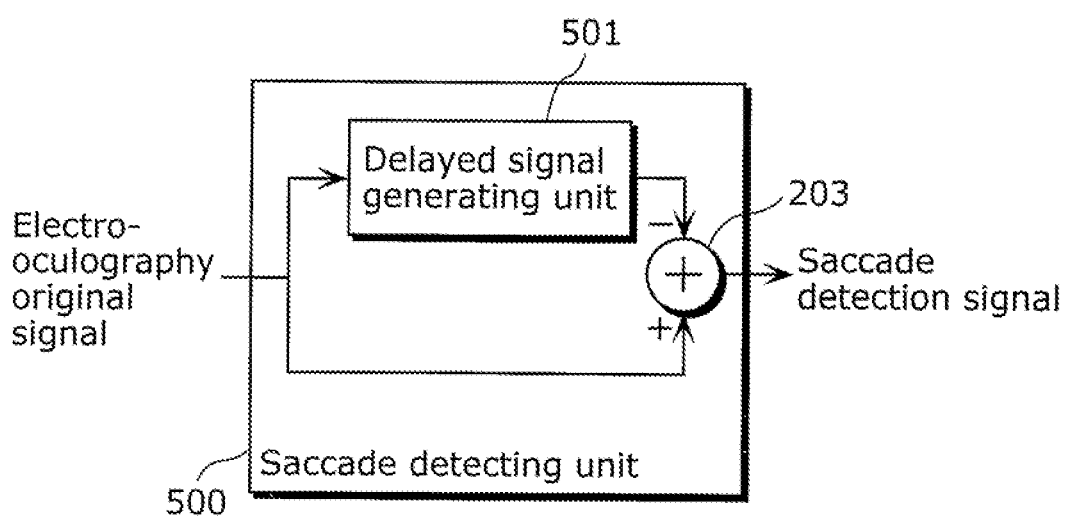
FIG. 21 is a block diagram of a second example of the saccade detecting unit according to the second embodiment of the present invention.

Next, FIG. 21 shows a block diagram of a saccade detecting unit 500 as another example of the saccade detecting unit according to the second embodiment.

The saccade detecting unit 500 according to the second embodiment includes a delayed signal generating unit 501 and the subtraction unit 203. The delayed signal generating unit 501 delays an electro-oculography original signal for a predetermined amount of time and outputs a delayed signal. In addition, an electro-oculogram original signal input into the saccade detecting unit 500 is branched into two signals. Then, one of the branched signals is input into the subtraction unit 203 as the delayed signal via the delayed signal generating unit 501 and the other is directly input into the subtraction unit 203. Then, the subtraction unit 203 subtracts the delayed signal from the electro-oculography original signal, to output a saccade signal. It is possible to easily obtain a plus and minus signed saccade signal by including the delayed signal generating unit 501.

Processing performed by the delayed signal generating unit 501 as shown in FIG. 21 will be described. The delayed signal generating unit 501 performs the following processing on an electro-oculography original signal f(x):

$$f\text{delay}(x) = f(x - t)$$

Figure 22:
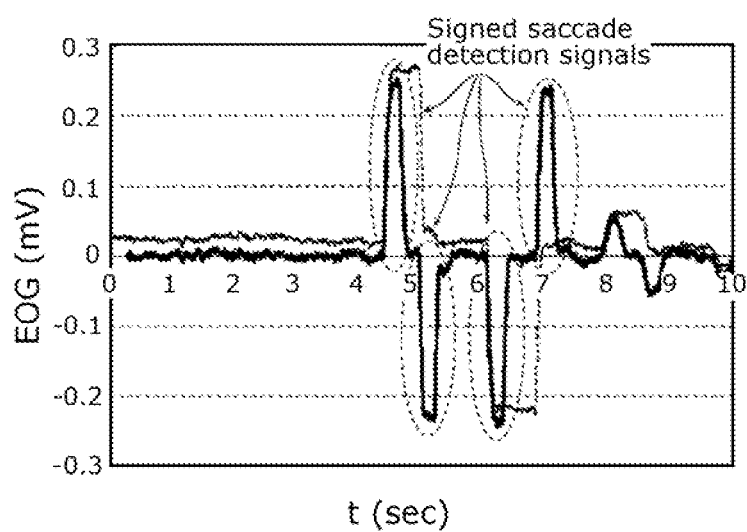
FIG. 22 is a diagram showing the saccade detection signal when a delay time for a delayed signal generating unit is 0.25 minutes.

Here, fdelay (x) is an electro-oculography signal after delay processing, and t is a delay time. The delayed signal can be obtained by performing the delay processing described above on the electro-oculography original signal shown in FIG. 12. Then, FIG. 22 shows an example where the subtraction unit 203 subtracts the delayed signal from the electro-oculography original signal. Note that, to detect a signed saccade component, the delay time is set to t=0.25 seconds. FIG. 22 shows that the signed saccade signal including the period of time during which the saccade occurred is obtained.

The saccade detecting unit 500 generates a saccade detection signal and an electro-oculography change amount based on an output signal from the subtraction unit 203 as shown in FIG. 22, to output the generated saccade detection signal and the electro-oculography change amount to the calibration index presenting unit 103 and the calibration parameter calculating unit 105. For example, when the amount of change in sampled values within a period of time corresponding to a period of time required for a saccadic movement exceeds a predetermined threshold, it is determined that a saccadic movement has occurred, so that a saccade detection signal is output. In addition, the amount of change in sampled values at this time is output as an electro-oculography change amount.

Figure 23:
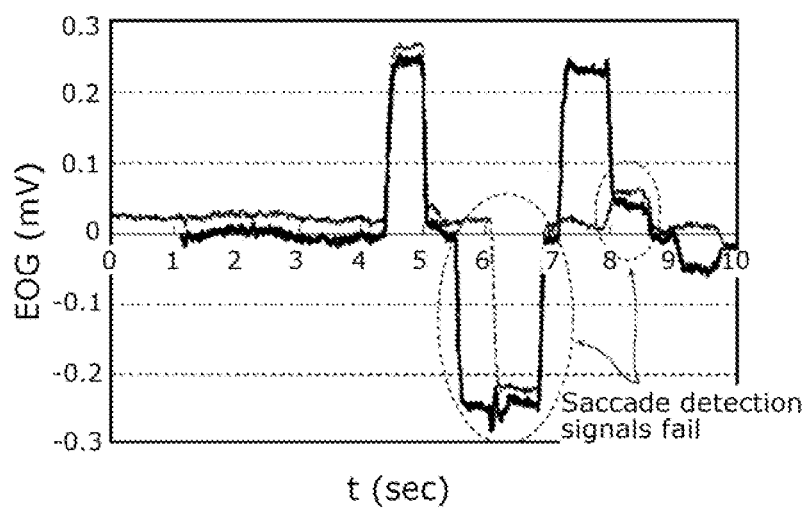
FIG. 23 is a diagram showing a saccade detection signal when a delay time for a delayed signal generating unit is 1.1 minutes.

Here, when the delay time t becomes larger than a general single fixation time=(approximately 0.3 to 0.4 seconds), the saccade signal fails as shown in FIG. 23. FIG. 23 is an example where the delay time t is 1.1 seconds. When the saccade signal fails as shown in FIG. 23, the saccade signal cannot be extracted. Thus, it is necessary to make the delay time t of the delayed signal generating unit 501 shorter than the general single fixation time. Note that, although the second embodiment has shown an example where the delay time of 0.25 seconds is applied, any value may be applied as long as the delay time is shorter than the general single fixation time.

With the configuration according to the second embodiment as described above, the configuration is effective in making it possible to distinguish between a plus and a minus signal by generating a delayed signal from an electro-oculography original signal to thereby detect a signed saccade signal.

<2. 3 Method of Removing Blink Signal>

Next, a calibration method considering an influence of blinking will be described.

Figure 24:
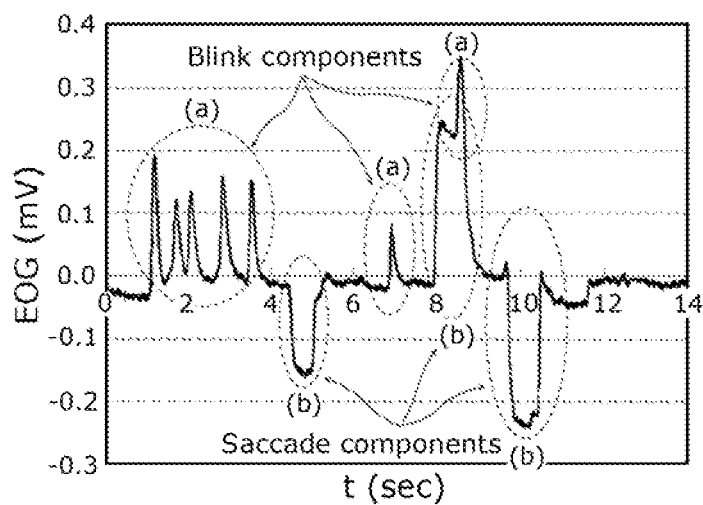
FIG. 24 is a diagram showing an example of an electro-oculography signal including a blink signal.

When the user blinks, as shown in a region (a) in FIG. 24, there is a case where a rapid potential (that is a "blink signal") is generated in a plus direction. For this reason, only with the method described above, it is not possible to detect only the saccade signal, thus causing degradation in calibration accuracy in some cases.

Figure 25:
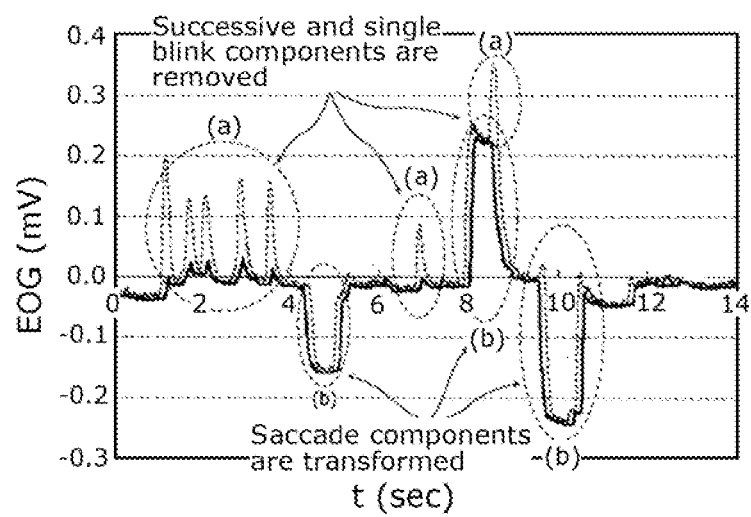
FIG. 25 is a diagram showing an electro-oculography signal obtained by applying minimum value filtering to the electro-oculography signal in FIG. 24.
Figure 26:
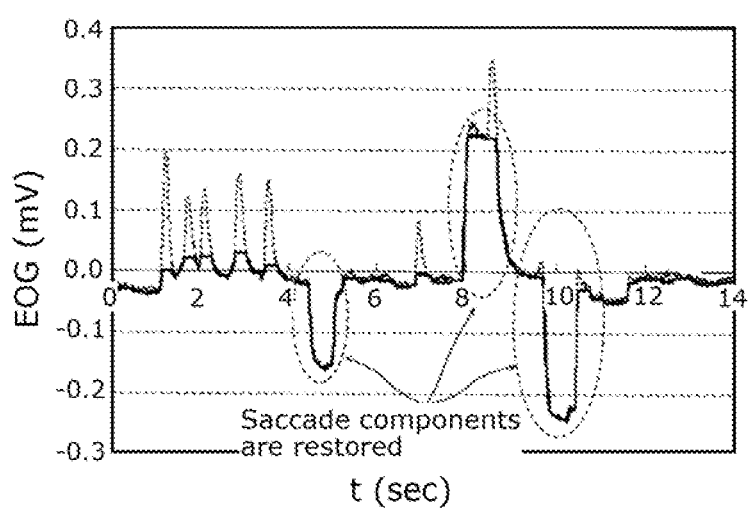
FIG. 26 is a diagram showing an electro-oculography signal obtained by applying maximum value filtering to the electro-oculography signal in FIG. 24.

Thus, the blink signal is removed by applying the minimum value filter as shown in FIG. 25. However, only with this, a portion indicating change in voltage by saccadic movement (saccade component) is transformed. Thus, by further applying the maximum value filter, the saccade component is restored as shown in FIG. 26.

Note that there is a case where the sign of the blink signal becomes minus depending on the attachment position of the electrode. When the blink signal is minus, the maximum value filter and the minimum value filter may be reversed in application order.

In addition, a filter length of the minimum value filter and the maximum value filter may be set to a value that is larger than a length of time for a general single blink (approximately 0.15 seconds to 0.2 seconds), and is smaller than a length of a single fixation time (approximately 0.3 seconds to 0.4 seconds).

In addition, in the case where only removing a blink signal is intended, only one of the minimum value filter and the maximum value filter may be applied.

As described above, the signal from which the blink signal is removed is input into the switch 106 shown in FIG. 4, as the electro-oculography original signal. This allows highly-accurate calibration without being affected by blinking. This removal of the blink signal is performed by a blink signal removing unit provided outside the eye-gaze tracking device 100 and is not shown in the figure.

Third Embodiment

Figure 27:
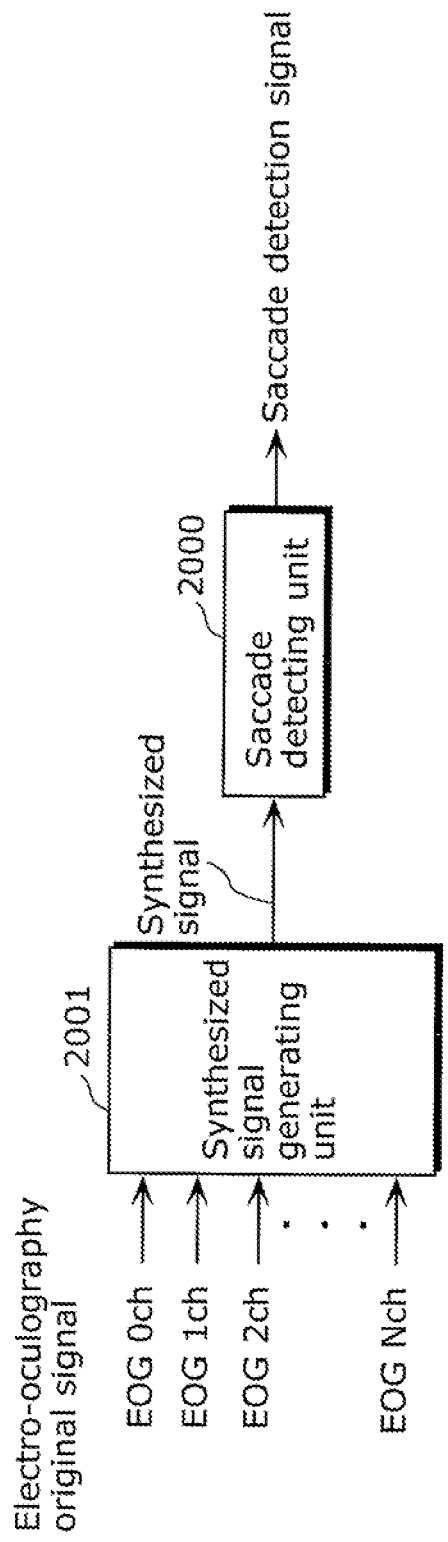
FIG. 27 is a block diagram of a saccade detecting unit according to a third embodiment of the present invention.

Next, FIG. 27 shows a block diagram showing a saccade detecting device according to a third embodiment. The third embodiment relates to the saccade detecting device when measuring electro-oculograms through multiple channels. The saccade detecting device is used in place of the saccade detecting unit 104 in the eye-gaze tracking device 100 according to the second embodiment as shown in FIG. 9.

The saccade detecting device according to the third embodiment includes a synthesized signal generating unit 2001 which generates a synthesized signal from the electro-oculography original signal through multiple channels, and a saccade detecting unit 2000.

Figure 28:
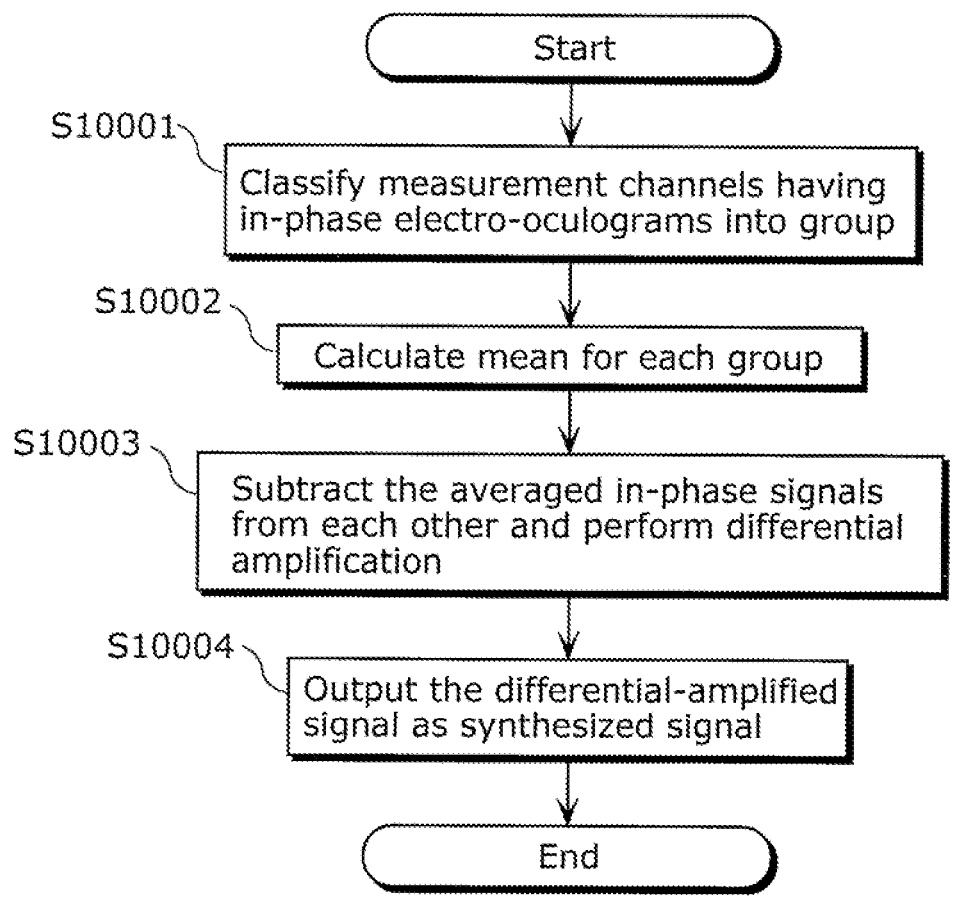
FIG. 28 is a flowchart showing an operation of a synthesized signal generating unit according to the third embodiment of the present invention.

For example, it is possible to consider that the synthesized signal generating unit 2001 generates a synthesized signal by performing: averaging using, from among electro-oculography original signals EOG0ch to EOGNch that have been input, electro-oculography signals of measurement channels through which the electro-oculograms are measured in phase with respect to the eyeball movement; and differential amplification after subtracting the averaged in-phase signals from each other. FIG. 28 shows a specific processing procedure.

First, grouping of measurement channels having in-phase electro-oculograms is performed (S10001). Here, whether the electro-oculograms are in phase or not can be judged according to the measurement position such as the right side and left side of the face. Note that the judgment may be performed not only by the measurement position but also be dynamically performed based on a feature of the measured electro-oculography signal. Next, averaging is performed on each group resulting from the grouping (S10002). Then, differential amplification is performed by subtracting in-phase signals from each other in each of the averaged groups (S10003), and the signals thus produced are output as a synthesized signal (S10004).

The saccade detecting unit 2000 generates a saccade detection signal, using the synthesized signal generated by the synthesized signal generating unit 2001. The process of generating the saccadic detection signal is performed in the same manner as the process performed by the saccade detecting unit 104 in the second embodiment.

The saccade detecting unit 2000 generates a saccade detection signal and amplitude information, and outputs the generated saccade detection signal and amplitude information to the calibration index presenting unit 103 and the calibration parameter calculating unit 105 shown in FIG. 9. For example, when an amount of change in sampled value within a period of time corresponding to an amount of time required for saccadic movement is above a predetermined threshold, it is judged that the saccadic movement has occurred, so that the saccade detection signal is output. In addition, the change amount of the sampled value at this time is output as amplitude information (electro-oculography change amount).

With the configuration according to the third embodiment as described above, since a synthesized signal having a high S/N ratio is generated from electro-oculography original signals through multiple channels, and a saccade signal is detected using the synthesized signal; thus, the configuration according to the third embodiment is effective in increasing accuracy in saccade detection.

Fourth Embodiment

Figure 29:
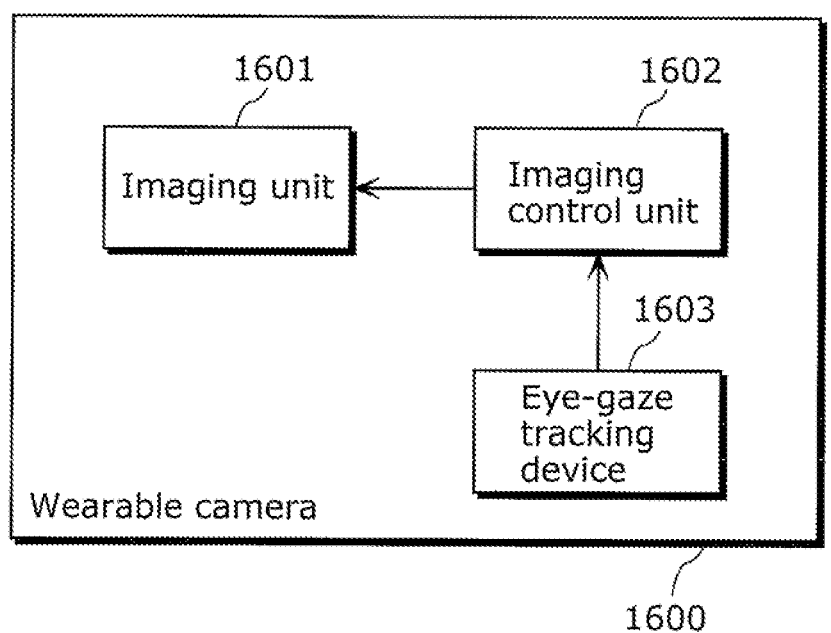
FIG. 29 is a block diagram of a wearable camera according to a fourth embodiment of the present invention.
Figure 30:
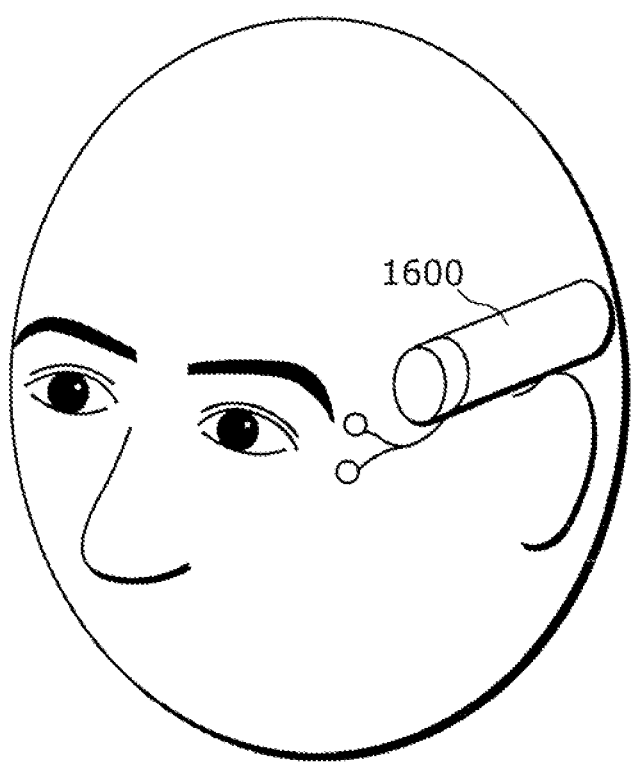
FIG. 30 is a diagram showing a state in which a user is wearing the wearable camera according to the fourth embodiment of the present invention.

Next, a wearable camera 1600 according to a fourth embodiment of the present invention will be described with reference to FIGS. 29 and 30. The wearable camera 1600, for example, is attached to a side of the user's head and captures an image in a gaze direction of the user. Specifically, the wearable camera 1600 includes: an imaging unit 1601, an imaging control unit 1602, and an eye-gaze tracking device 1603.

The wearable camera 1600 may be, for example, a camera which captures a still image or a video camera which captures video. To the eye-gaze tracking device 1603, for example, it is possible to apply the eye-gaze tracking device 1 according to the first embodiment or the eye-gaze tracking device 100 according to the second embodiment. In addition, the electrode as an electro-oculography measuring unit in the fourth embodiment is attached to the user, as shown in FIG. 30, on upper and lower sides of the temple beside the left eye.

Then, the imaging control unit 1602 monitors an output signal from the eye-gaze tracking device 1603, and changes an orientation of the imaging unit 1601 following the movement of the user's gaze. This allows the imaging unit 1601 to capture the gaze direction of the user.

However, the wearable camera 1600 according to the fourth embodiment is not limited to the use as described above. For other uses, it is also possible to apply the wearable camera 1600 to devices such as a device which plots the user's gaze position detected by the eye-gaze tracking device 1603 on the image captured by the imaging unit 1061, or a device which detects the gaze of a driver to alert danger while driving, or the like.

Fifth Embodiment

Figure 31:
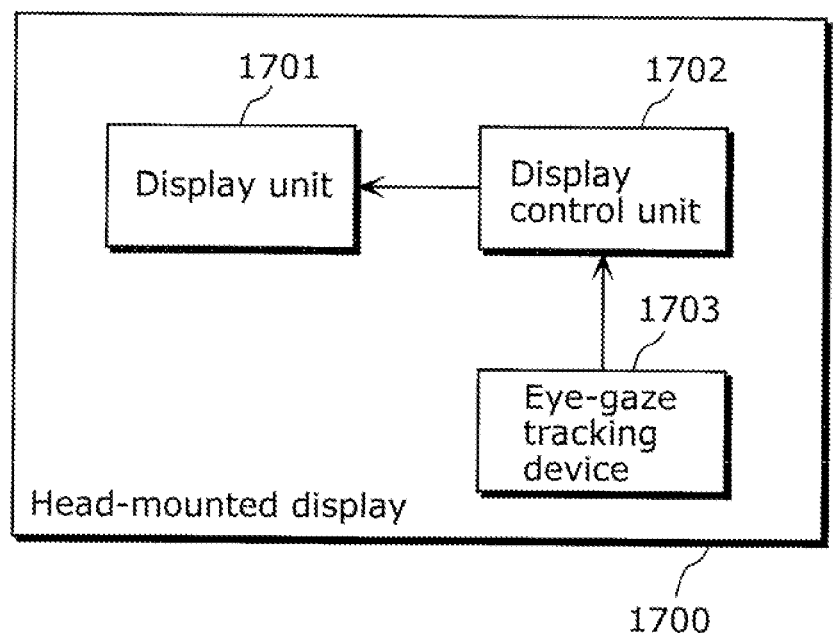
FIG. 31 is a block diagram of a head-mounted display according to a fifth embodiment of the present invention.
Figure 32:
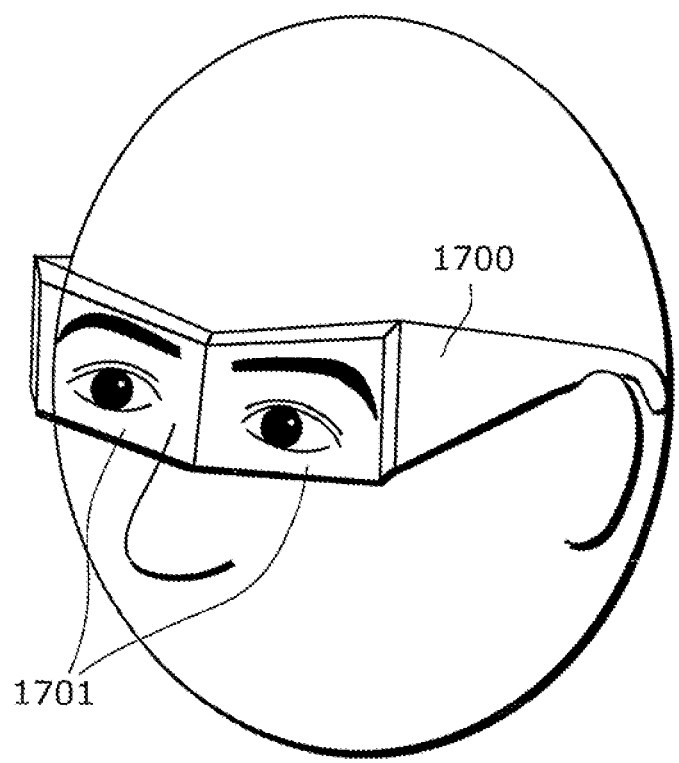
FIG. 32 is a diagram showing a state in which a user is wearing the head-mounted display according to the fifth embodiment of the present invention.

Next, a head-mounted display 1700 according to a fifth embodiment of the present invention will be described with reference to FIGS. 31 and 32. The head-mounted display 1700, for example, has an eyeglass shape, and is a device which displays an image in front of the user's eyes, and moves a mouse pointer that is shown on the displayed image into the user's gaze direction. Specifically, the head-mounted display 1700 includes a display unit 1701, a display control unit 1702, and an eye-gaze tracking device 1703.

Figure 33:
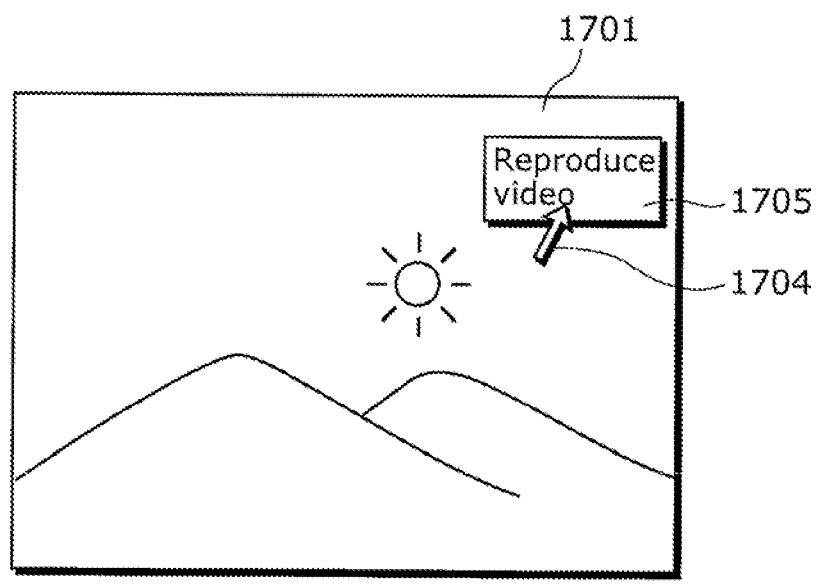
FIG. 33 is a diagram showing an example of an image displayed in a display unit of the head-mounted display according to the fifth embodiment of the present invention.

As shown in FIG. 33, it is assumed that various images are displayed on the display unit 1701, and a mouse pointer 1704 is displayed on such images. To the eye-gaze tracking device 1703, for example, it is possible to apply the eye-gaze tracking device 1 according to the first embodiment or the eye-gaze tracking device 100 according to the second embodiment.

Then, the display control unit 1702 monitors an output signal from the eye-gaze tracking device 1703, and moves the mouse pointer 1704 that is displayed on the display unit 1701, following the movement of the user's gaze. This allows, for example, a processing executing unit (not shown in the figure) to execute processing associated with an icon 1705 (video reproduction processing in the example shown in FIG. 33) pointed by the mouse pointer 1704.

Sixth Embodiment

Figure 34:
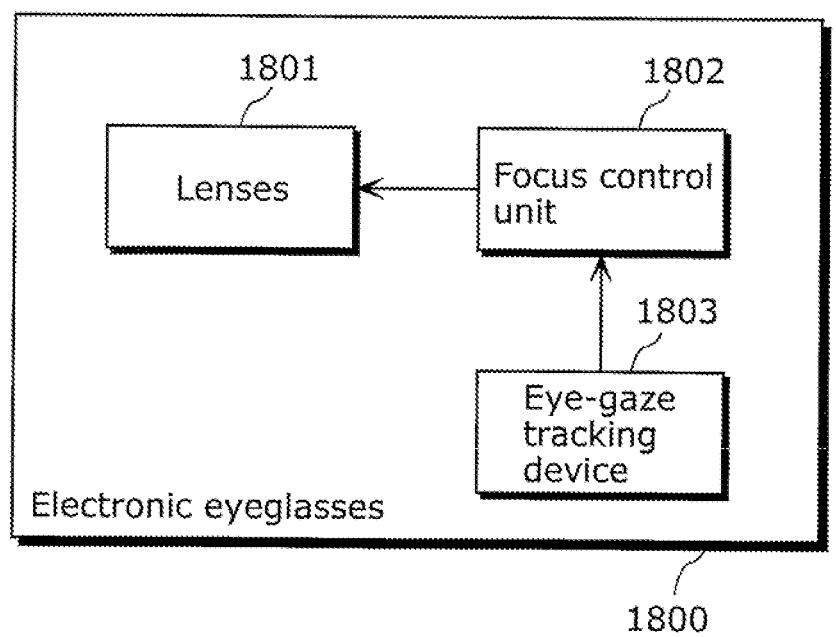
FIG. 34 is a block diagram of electronic eyeglasses according to a sixth embodiment of the present invention.
Figure 35:
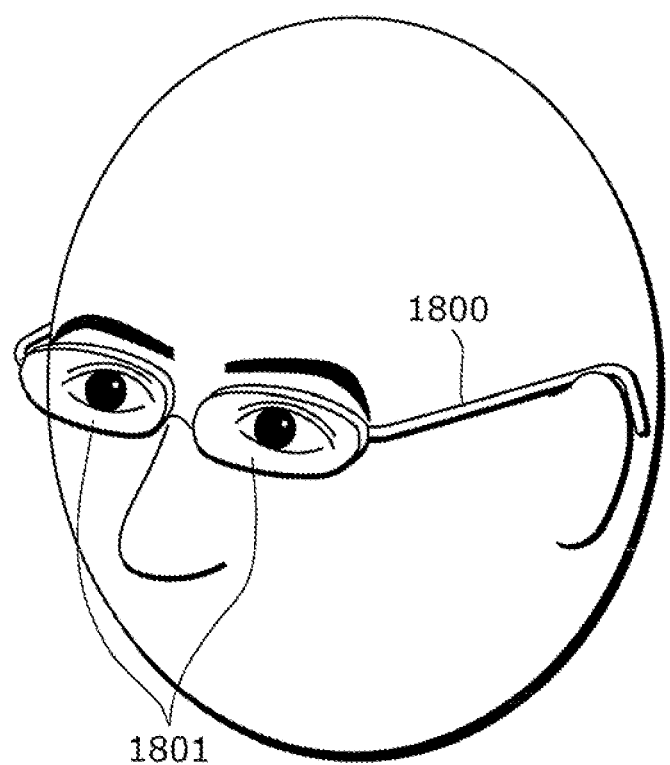
FIG. 35 is a diagram showing a state in which the user is wearing the electronic eyeglasses according to the sixth embodiment of the present invention.

Next, electronic eyeglasses 1800 according to a sixth embodiment of the present invention will be described with reference to FIGS. 34 and 35. The electronic eyeglasses 1800 are eyeglasses capable of changing a focal point of each lens according to the user's gaze position. Specifically, the electronic eyeglasses 1800 include: lenses 1801, a focus control unit 1802, and an eye-gaze tracking device 1803.

Each lens 1801 is located before an eye of the user, and can electronically change the focal point.

To the eye-gaze tracking device 1803, for example, it is possible to apply the eye-gaze tracking device 1 according to the first embodiment or the eye-gaze tracking device 100 according to the second embodiment.

Then, the focus control unit 1802 monitors an output signal from the eye-gaze tracking device 1803, and changes the focal point of each lens 1801, following the movement of the user's gaze. For example, when the user is taking a close look at a book to read or the like, the focus control unit 1802 controls the focal point of each lens 1801 so as to focus each lens 1801 at a closer point. In addition, when the user is looking at a landscape in the distance, the focus control unit 1802 controls the focal point of each lens 1801 so as to focus each lens 1801 at a distant point.

Note that in the present embodiment, it is assumed that the right and left eyes of the user are gazing at the same point. This allows the eye-gaze tracking device 1803 to detect the gaze position from the electro-oculogram.

Other Embodiment

In the embodiments described above, respective blocks may be individually configured into one chip using a semiconductor device such as LSI, or may include one chip so as to include part or all of the blocks. Note that what is referred to as LSI here is also referred to as: IC, system LSI, super LSI, and ultra LSI.

In addition, the circuit integration technique may be realized not only by LSI but also by a dedicated circuit or a general-purpose processor. After manufacturing an LSI, a Field Programmable Gate Array (FPGA) that is programmable or a reconfigurable processor that allows reconfiguration of connections and settings of circuit cells in the LSI may be used.

Furthermore, when another circuit integration technique appears to replace the LSI as a result of progress in semiconductor technology or another derivative technique, the technique may naturally be used to integrate function blocks. Application of biotechnology and so on is one of the possibilities.

In addition, each process in the above embodiments may be realized using hardware or software. Furthermore, the above embodiments may be realized by mixed processing by software and hardware. Note that it goes without saying that adjustment of timing for performing each process is necessary in the case of realizing, using hardware, the wearable camera according to the above embodiments. In the above embodiments, for convenience of description, details of timing adjustment for different types of signals, which is required in actual hardware designing, are omitted.

In the case of realizing each process in the above embodiments using software, each process is realized by executing a program on a computer having a general configuration such as CPU and RAM. The program like this may be recorded on a non-volatile computer-readable recording medium.

Figure 36:
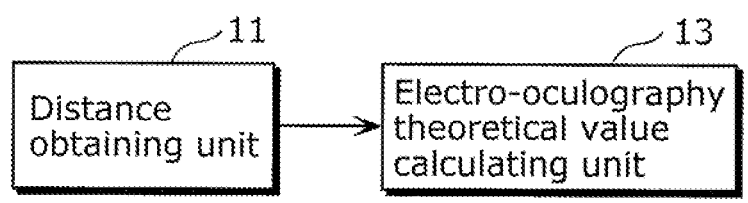
FIG. 36 is a block diagram showing essential constituent elements of the present invention.

FIG. 36 is a diagram showing essential constituent elements according to the present invention; in the case of realizing the present invention as an electro-oculography estimating device, the electro-oculography estimating device includes the distance obtaining unit 11 and the electro-oculography theoretical value calculating unit 13. The distance obtaining unit 11 and the electro-oculography theoretical value calculating unit 13 have the same configuration, respectively, as the distance obtaining unit 11 and the electro-oculography theoretical value calculating unit 13 that are shown FIG. 1.

Note that a specific configuration according to the present invention is not limited to the embodiments described earlier, but may be changed or modified in various ways within the scope not departing from the present invention.

Although only some exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

INDUSTRIAL APPLICABILITY

Since an electro-oculography estimating device according to the present invention allows calculating an electro-oculogram with high accuracy, it is possible to apply the electro-oculography estimating device to an analysis of the electro-oculogram in the electrophysiological field. In addition, since an eye-gaze tracking device according to the present invention allows detecting a three-dimensional gaze position (gaze point) including a depth direction with high accuracy, it is expected to apply the eye-gaze tracking device as an interface or the like to various devices such as a wearable device (for focus control in a wearable camera, head-mounted display, or electronic eyeglasses).

What is claimed is:

1. An electro-oculography estimating device which estimates an electro-oculography theoretical value that is a theoretical value of an electro-oculogram generated in a living body, said electro-oculography estimating device comprising:
  a distance obtaining unit configured to obtain (i) a right-eye corneal distance and a right-eye retinal distance each of which is a distance to an arbitrary three-dimensional spatial position from a corresponding one of a right eye cornea and a right eye retina, and (ii) a left-eye corneal distance and a left-eye retinal distance each of which is a distance to the arbitrary three-dimensional spatial position from a corresponding one of a left eye cornea and a left eye retina; and
  an electro-oculography theoretical value calculating unit configured to calculate the theoretical value of the electro-oculogram generated at the arbitrary three-dimensional spatial position, using, as input into an electro-oculography model, the right-eye corneal distance, the right-eye retinal distance, the left-eye corneal distance, and the left-eye retinal distance obtained by said distance obtaining unit, the electro-oculography model being a function for calculating the electro-oculography theoretical value generated at the arbitrary three-dimensional spatial position.

2. The electro-oculography estimating device according to claim 1,
  wherein, based on an assumption that a right eye and a left eye are gazing at a same gaze point, said distance obtaining unit is configured to calculate the right-eye corneal distance, the right-eye retinal distance, the left-eye corneal distance, and the left-eye retinal distance, based on a parallel movement component of both eyes, and a depth distance from both of the eyes to the same gaze point or a vergence movement component of both of the eyes.

3. The electro-oculography estimating device according to claim 1,
  wherein the electro-oculography model includes predetermined coefficients each of which is individually settable for a corresponding one of the right-eye corneal distance, the right-eye retinal distance, the left-eye corneal distance, and the left-eye retinal distance.

4. The electro-oculography estimating device according to claim 3,
  wherein, in the electro-oculography model, when: $r_1$, $r_2$, $r_3$, and $r_4$ represent, respectively, the right-eye corneal distance, the right-eye retinal distance, the left-eye corneal distance, and the left-eye retinal distance; $f_1$, $f_2$, $f_3$, and $f_4$ represent, respectively, a function for converting the right-eye corneal distance, the right-eye retinal distance, the left-eye corneal distance, and the left-eye retinal distance into the electro-oculogram; and $\alpha_1$, $\alpha_2$, $\alpha_3$, and $\alpha_4$ represent, respectively, the predetermined coefficients each of which is settable for the corresponding one of the right-eye corneal distance, the right-eye retinal distance, the left-eye corneal distance, and the left-eye retinal distance, and when the electro-oculography theoretical value is represented by $$\hat{v}, \quad [\text{Math 1}]$$

$\alpha_1$ and $\alpha_2$ are not zero at the same time, and $\alpha_3$ and $\alpha_4$ are not zero at the same time, in accordance with:

$$\hat{v} = \alpha_1 f_1(r_1) + \alpha_2 f_2(r_2) + \alpha_3 f_3(r_3) + \alpha_4 f_4(r_4). \quad [\text{Math 2}]$$

5. The electro-oculography estimating device according to claim 4, wherein the electro-oculography model is represented by:

$$\hat{v} = \alpha_1/r_1 + \alpha_2/r_2 + \alpha_3/r_3 + \alpha_4/r_4. \quad [\text{Math 3}]$$

6. The electro-oculography estimating device according to claim 4, further comprising
  a model parameter estimating unit configured to estimate the predetermined coefficients $\alpha_1$, $\alpha_2$, $\alpha_3$, and $\alpha_4$ each of which is obtained for a corresponding one of a plurality of gaze positions so that a difference between a theoretical voltage and an observation voltage is smallest, the theoretical voltage being generated at a corresponding one of a plurality of electrodes provided at different positions and calculated using the electro-oculography model, and the observation voltage being observed at the plurality of electrodes.

7. The electro-oculography estimating device according to claim 6,
  wherein, when, for each of the plurality of electrodes i (i=1, ..., N): $\Delta v_i = (\Delta v_{i,1}, \ldots, \Delta v_{i,M})^t$ represents the observation voltage at a corresponding one of M different gaze positions $\theta_j$ (j=1, ..., M); $\alpha_i = (\alpha_{i,1}, \alpha_{i,2}, \alpha_{i,3}, \alpha_{i,4})^t$ represents the predetermined coefficients each of which is settable for the corresponding one of the right-eye corneal distance, the right-eye retinal distance, the left-eye corneal distance, and the left-eye retinal distance; $r_{i,j,1}$, $r_{i,j,2}$, $r_{i,j,3}$, and $r_{i,j,4}$, represent, respectively, the right-eye corneal distance, the right-eye retinal distance, the left-eye corneal distance, and the left-eye retinal distance; and $f_{i,1}$, $f_{i,2}$, $f_{i,3}$, and $f_{i,4}$ represent, respectively, the function for converting the right-eye corneal distance, the right-eye retinal distance, the left-eye corneal distance, and the left-eye retinal distance, and when a matrix $A_i$ is represented by $$A_i = \begin{pmatrix} f_{i,1}(r_{i,1,1}) & f_{i,2}(r_{i,1,2}) & f_{i,3}(r_{i,1,3}) & f_{i,4}(r_{i,1,4}) \\ \vdots & \vdots & \vdots & \vdots \\ f_{i,1}(r_{i,M,1}) & f_{i,2}(r_{i,M,2}) & f_{i,3}(r_{i,M,3}) & f_{i,4}(r_{i,M,4}) \end{pmatrix} \quad [\text{Math 4}]$$

and when, for a reference electrode R: $\alpha_R = (\alpha_{R,1}, \alpha_{R,2}, \alpha_{R,3}, \alpha_{R,4})^t$ represents the predetermined coefficients each of which is settable for the corresponding one of the right-eye corneal distance, the right-eye retinal distance, the left-eye corneal distance, and the left-eye retinal distance at the corresponding one of the M different gaze positions $\theta_j$ (j=1, ..., M); $r_{R,1,1}$, $r_{R,i,2}$, $r_{R,i,3}$, and $r_{R,i,4}$ represent, respectively, the right-eye corneal distance, the right-eye retinal distance, the left-eye corneal distance, and the left-eye retinal distance; and $f_{R,1}$, $f_{R,2}$, $f_{R,3}$, and $f_{R,4}$ represent, respectively, the function for converting the right-eye corneal distance, the right-eye retinal distance, the left-eye corneal distance, and the left-eye retinal distance, and when a matrix $A_R$ is represented by $$A_R = \begin{pmatrix} f_{R,1}(r_{R,1,1}) & f_{R,2}(r_{R,1,2}) & f_{R,3}(r_{R,1,3}) & f_{R,4}(r_{R,1,4}) \\ \vdots & \vdots & \vdots & \vdots \\ f_{R,1}(r_{R,M,1}) & f_{R,2}(r_{R,M,2}) & f_{R,3}(r_{R,M,3}) & f_{R,4}(r_{R,M,4}) \end{pmatrix} \quad \text{[Math 5]}$$

said model-parameter estimating unit is configured to calculate each of the predetermined coefficients $\alpha_i$ and $\alpha_R$ for the plurality of electrodes and the reference electrode, in accordance with:

$$\alpha_R = -\left(A_R^t \left(\sum_{i=1}^N B_i\right) A_R\right)^{-1} A_R^t \left(\sum_{i=1}^N B_i \Delta v_i\right) \quad \text{[Math 6]}$$

$$\alpha_i = (A_i^t A_i)^{-1} A_i^t (A_R \alpha_R + \Delta v_i)$$

(However, $B_i = A_i(A_i^t A_i)^{-1} A_i^t - I$, where I is a unit matrix).

8. The electro-oculography estimating device according to claim 6,
wherein said model-parameter estimating unit is configured to estimate the predetermined coefficients $\alpha_1$, $\alpha_2$, $\alpha_3$, and $\alpha_4$, using the observation voltage at the plurality of electrodes, the observation voltage being observed during eyeball movement that moves in a front-rear direction with respect to the living body from which the electro-oculogram is to be measured.

9. The electro-oculography estimating device according to claim 6,
wherein said model-parameter estimating unit is configured to estimate the predetermined coefficients $\alpha_1$, $\alpha_2$, $\alpha_3$, and $\alpha_4$, using the observation voltage at the plurality of electrodes, the observation voltage being obtained by saccadic movement.

10. The electro-oculography estimating device according to claim 1,
wherein the electro-oculography model is configured using a look-up table indicating a correspondence relationship between the electro-oculography theoretical value and a gaze direction of a user.

11. The electro-oculography estimating device according to claim 1, further comprising
at least one electrode which is provided between both eyes of a user, measures the electro-oculogram, and outputs an electro-oculography original signal.

12. The electro-oculography estimating device according to claim 11,
wherein said at least one electrode is incorporated in a frame of eyeglasses, and includes a plurality of electrodes each of which is provided at a position at which the eyeglasses contact skin.

13. The electro-oculography estimating device according to claim 1, further comprising
a plurality of electrodes each of which is positioned in front and back of an ear, measures the electro-oculogram, and outputs an electro-oculography original signal.

14. An electro-oculography calculating method for calculating, by an electro-oculography calculating device, a theoretical value of an electro-oculogram generated in a living body, said electro-oculography calculated method comprising:
obtaining (i) a right-eye corneal distance and a right-eye retinal distance each of which is a distance to an arbitrary three-dimensional spatial position from a corresponding one of a right eye cornea and a right eye retina, and (ii) a left-eye corneal distance and a left-eye retinal distance each of which is a distance to the arbitrary three-dimensional spatial position from a corresponding one of a left eye cornea and a left eye retina; and calculating the theoretical value of the electro-oculogram generated at the arbitrary three-dimensional spatial position, using, as input into an electro-oculography model, the right-eye corneal distance, the right-eye retinal distance, the left-eye corneal distance, and the left-eye retinal distance obtained in said obtaining, the electro-oculography model being function for calculating the theoretical value of the electro-oculogram generated at the arbitrary three-dimensional spatial position.

15. An eye-gaze tracking device which detects a gaze direction of a user based on an electro-oculogram, said eye-gaze tracking device comprising:
an electro-oculography measuring unit configured to measure the electro-oculogram generated by eyeball movement, and outputs an electro-oculography original signal;

a calibration index presenting unit configured to present a calibration index to the user;

a saccade detecting unit configured to detect saccadic movement and output an electro-oculography change amount that is an amount of change in the electro-oculogram before and after the saccadic movement, the saccadic movement being rapid eyeball movement that occurs when a gaze position of the user moves to the calibration index presented by said calibration index presenting unit;

a calibration parameter calculating unit configured to calculate predetermined coefficients of an electro-oculography model based on a position of the calibration index presented by said calibration index presenting unit and the electro-oculography change amount that is output from said saccade detecting unit, using (i) a right-eye corneal distance and a right-eye retinal distance each of which is a distance to an arbitrary three-dimensional spatial position from a corresponding one of a right-eye cornea and a right-eye retina, (ii) a left-eye corneal distance and a left-eye retinal distance each of which is a distance to the arbitrary three-dimensional spatial position from a corresponding one of a left-eye cornea and a left-eye retina; and (iii) the predetermined coefficients, the electro-oculography model being a function for calculating the theoretical value of the electro-oculogram generated at the arbitrary three-dimensional spatial position, and the predetermined coefficients being individually settable for a corresponding one of the right-eye corneal distance, the right-eye retinal distance, the left-eye corneal distance, and the left-eye retinal distance; and a calibration unit configured to detect the gaze direction of the user from the electro-oculogram, based on the electro-oculography model.

16. The eye-gaze tracking device according to claim 15,
wherein said saccade detecting unit includes:
a delayed signal generating unit configured to delay the electro-oculography original signal for a predetermined delay time and output a delayed signal;

a subtraction unit configured to generate an output signal obtained by subtracting the delayed signal from the electro-oculography original signal; and a saccade determination unit configured to determine that a signal larger than a predetermined threshold is a saccade signal representing the saccadic movement, the signal being included in the output signal, and the predetermined delay time is shorter than a period of time for which the user is gazing at the calibration index.

17. A wearable camera which captures an image in a gaze direction of a user, said wearable camera comprising:

an imaging unit;

the eye-gaze tracking device according to claim 15; and an imaging control unit configured to cause said imaging unit to capture the image in the gaze direction detected by said eye-gaze tracking device.

18. A head-mounted display which moves a mouse pointer in a gaze direction of a user, said head-mounted display comprising:

a display unit configured to display an image and the mouse pointer;

the eye-gaze tracking device according to claim 15; and a display control unit configured to move the mouse pointer in the gaze direction detected by said eye-gaze tracking device, the mouse pointer being displayed on the display unit.

19. Electronic eyeglasses which change a focal point of each of lenses according to a gaze position of a user, said electronic eyeglasses comprising:

lenses each having a changeable focal point;

the eye-gaze tracking device according to claim 15; and a focus control unit configured to change the focal point of each of said lenses according to the gaze position detected by said eye-gaze tracking device.

20. A non-transitory computer readable medium having stored thereon a program for calculating a theoretical value of an electro-oculogram generated in a living body, said program causing a computer to execute:

obtaining (i) a right-eye corneal distance and a right-eye retinal distance each of which is a distance to an arbitrary three-dimensional spatial position from a corresponding one of a right eye cornea and a right eye retina, and (ii) a left-eye corneal distance and a left-eye retinal distance each of which is a distance to the arbitrary three-dimensional spatial position from a corresponding one of a left eye cornea and a left eye retina; and calculating the theoretical value of the electro-oculogram generated at the arbitrary three-dimensional spatial position, using, as input into an electro-oculography model, the right-eye corneal distance, the right-eye retinal distance, the left-eye corneal distance, and the left-eye retinal distance obtained in the obtaining, the electro-oculography model being a function for calculating the theoretical value of the electro-oculogram generated at the arbitrary three-dimensional spatial position.

* * * * *